US008158442B2

(12) United States Patent
Bufe et al.

(10) Patent No.: US 8,158,442 B2
(45) Date of Patent: Apr. 17, 2012

(54) ANTAGONISTS OF BITTER TASTE RECEPTORS AND USES THEREOF

(75) Inventors: Bernd Bufe, Ferch (DE); Christina Kuhn, Nuthetal (DE); Wolfgang Meyerhof, Norderstedt (DE)

(73) Assignee: Deutsches Institut Fuer Ernaehrungsforschung Potsdam-Rehbruecke-Stiftung Des Oefentlichen Rechts, Nuthetal (DE)

( * ) Notice: Subject to any disclaimer, the term of this patent is extended or adjusted under 35 U.S.C. 154(b) by 0 days.

(21) Appl. No.: 12/596,434

(22) PCT Filed: Apr. 18, 2008

(86) PCT No.: PCT/EP2008/003156
§ 371 (c)(1),
(2), (4) Date: Dec. 23, 2009

(87) PCT Pub. No.: WO2008/128730
PCT Pub. Date: Oct. 30, 2008

(65) Prior Publication Data
US 2010/0113548 A1 May 6, 2010

Related U.S. Application Data

(60) Provisional application No. 60/923,994, filed on Apr. 18, 2007.

(30) Foreign Application Priority Data

Apr. 18, 2007 (EP) .................................... 07007910

(51) Int. Cl.
*G01N 33/567* (2006.01)
(52) U.S. Cl. .......... 436/501; 435/7.1; 435/7.2; 435/7.21
(58) Field of Classification Search .................. None
See application file for complete search history.

(56) References Cited

U.S. PATENT DOCUMENTS

| 2007/0037134 A1 | 2/2007 | Servant et al. |
| 2008/0038739 A1 | 2/2008 | Li et al. |
| 2008/0213761 A1 | 9/2008 | Bufe et al. |

FOREIGN PATENT DOCUMENTS

| WO | 03/008627 | 1/2003 |
| WO | 2004029087 | 4/2004 |
| WO | 2005102311 | 11/2005 |
| WO | 2006/053771 | 5/2006 |

OTHER PUBLICATIONS

International Search Report for PCT/EP2008/003156, dated Aug. 4, 2008 (8 pages).
Miguet, Laurence et al., "Computational studies of ligand-receptor interactions in bitter taste receptors", Journal of Receptor and Signal Transduction Research, Marcel Dekker, New Yor, NY, U.S., vol. 26, 20 5-6, 2006, pp. 611-630, XP009090670, ISSN: 1079-9893.
Bufe, B et al., "The Molecular Basis of Individual Differences in Phenylthiocarbamide and Propylthioracil Bitterness Perception", Current Biology, Current Science, GB, vol. 15, No. 4, Feb. 22, 2005, pp. 322-327, XP004758977, ISSN: 0960-9822.
Caicedo, A. et al., "Taste Receptor Cells That Discriminate Between Bitter Stimuli" (2001) Science 291: 1557-1560.
Dulac, C. "The Physiology of Taste, Vintage 2000" (2000) Cell 100: 607-610.
Kinnamon, S. "A Plethora of Taste Receptors" (2000) Neuron 25: 507-510.
Lindemann, B. "Receptors and transduction in taste" (2001) Nature 413: 219-225.
Margolskee, R. "Molecular Mechanisms of Bitter and Sweet Taste Transduction" (2001) J. Biol. Chem. 277: 1-4.
Drewnowski et al., "The Science and Complexity of Bitter Taste," 2001, Nutr. Rev. 59: 163-169.
Chandrasheka et al., "T2Rs Function as Bitter Taste Receptors" (2000) Cell 100: 703-711.
Matsunami et al "A family of candidate taste receptors in human and mouse" (2000) Nature 404: 601-604.
Adler et al., "A Novel Family of Mammalian Taste Receptors" (2000) Cell 100: 693-702.
Bufe et al., "The human TAS2R16 receptor mediates bitter taste in response to ss-glucopyranosides," (2002) Nature.
Duffy et al., "Bitter Receptor Gene (TAS2R38), 6-n-Propylthiouracil (PROP) Bitterness and Alcohol Intake," (2004) Alcohol Clin Exp Res. 28(11): 1629-1637.
McClintock T. et al., "Functional expression of recombinant G-protein coupled receptors monitored by video imaging of pigment movement in melanophores" (1993) Anal. Biochem. 209: 298-305.
McClintock et al., "Functional analysis by imaging of melanophore pigment dispersion of chimeric receptors constructed by recombinant polymerase chain reaction" (1997) Bran Res. Brain, Res. Protoc. 2: 59-68.
Potenza MN et al "A Rapid Quantitative Bioassay for Evaluating the Effects of Ligands Upon Receptors That Modulate cAMP Levels in a Melanophore Cell Line" (1992) Pigment Cell Res. 5:372-328.
Karlin et al., "Applications and statistics for multiple high-scoring segments in molecular sequences" (1993) Proc. Natl. Acad. Sci USA 90: 5873-5877.
Altschul et al "Basic Local Alignment Search Tool" (1990) J. Mol. Biol. 215: 403-410.
Altschul et al. "Gapped BLAST and PSI-BLAST: a new generation of protein database search programs" (1997) Nucleic Acids Res. 25: 3389-3402.
Carlezon et al "Herpes Simplex virus-mediated gene transfer as a tool for neuropsychiatric research" (2000) Crit. Rev. Neurobiol. 14: 47-67.
Carter et al. "Adeno-associated viral vectors as gene delivery vehicles" (2000) U. Mol. Med. 6: 17-27.

(Continued)

*Primary Examiner* — John Ulm
(74) *Attorney, Agent, or Firm* — Baker Donelson Bearman Caldwell & Berkowitz PC

(57) ABSTRACT

The present invention relates to antagonists of the human bitter-taste receptors hTAS2R[38]. The invention also relates to methods for identifying further molecules that suppress hTAS2R[38] mediated bitter taste transduction or bitter taste response and uses thereof.

9 Claims, 3 Drawing Sheets

OTHER PUBLICATIONS

Figure 1:
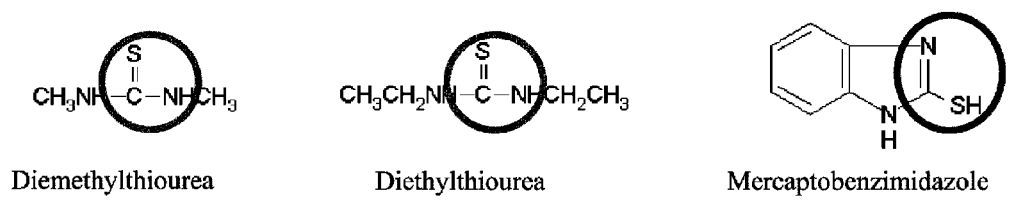

Kobinger et al "Filovirus-pseudotyped lentiviral vector can efficiently and stably transduce airway epithelia in vivo" (2001) Nat. Biotechnol. 19: 225-30.

Lindmann, B., "Sodium taste," Nephrology and Hypertension 1997, 6: 425-429.

Springer et al. "VEGF Gene Delivery to Muscle: Potential Role for Vasculogenesis in Adults" (1998) Mol. Cell 2: 549-58.

Chang et al (2001) Curr. Gene Therap. 1: 237-251.

Miguet et al., "Computational Studies of Ligand-Receptor Interactions in Bitter Tastes Receptors," Journal of Receptors and Signal Transduction Research, XP009090670, 2006, 611-630, vol. 26.

Bufe et al., "The Molecular Basis of Individual Differences in Phenylthiocarbamide and Propylthiouracil Bitterness Perception," Current Biology, Feb. 22, 2005, 322-327, vol. 15.

Search Report of Application No. 200906876-8 completed Sep. 26, 2010.

Written Opinion of Application No. 200906876-8 mailed Feb. 11, 2011.

Diemethylthiourea    Diethylthiourea    Mercaptobenzimidazole

ANTAGONISTS OF BITTER TASTE RECEPTORS AND USES THEREOF

CROSS REFERENCE TO RELATED APPLICATIONS

This application is a §371 National Stage Application of PCT/EP2008/003156 filed Apr. 18, 2008, which claims priority to European Application 070065910.8 filed Apr. 18, 2007, and U.S. Application 60/923,994 filed Apr. 18, 2007.

The present invention relates to antagonists of the human bitter-taste receptors hTAS2R38. The invention also relates to methods for identifying further molecules that suppress hTAS2R38 mediated bitter taste transduction or bitter taste response and uses thereof.

BACKGROUND OF THE INVENTION

1. Field of the Invention

Investigators have recently turned their attention to understanding the biological mechanisms of taste, and in particular bitter taste. For a review of the literature see, for example, Caicedo A. and Roper S D. (2001) Science 291: 1557-1560; Dulac C. (2000) Cell 100: 607-610; Kinnamon S. C. (2000) Neuron 25: 507-510; Lindemann B. (2001) Nature 413: 219-225; and Margolskee R F. (2001) J. Biol. Chem. 277: 1-4.

2. Description of Related Art

Bitter taste is aversive, and as such provides humans with a mechanism of protection against poisonous substances, which are generally bitter-tasting compounds. More subtly, bitter-tastants also affect the palatability of food, beverages, thereby influencing human nutritional habits as is more fully discussed by Drewnowski in "The Science and Complexity of Bitter Taste", (2001) Nutr. Rev. 59: 163-169. They also affect the palatability of other ingestibles such as orally administered pharmaceuticals and nutraceuticals. Understanding the mechanism of bitter taste transduction has implications for the food and pharmaceutical industries. If the bitter taste transduction pathway can be manipulated, it may be possible to suppress or eliminate bitter taste to render foods more palatable and increase patient compliance with oral pharmaceutics.

Taste transduction involves the interaction of molecules, i.e. tastants with taste receptor-expressing cells which reside in the taste buds located in the papillae of the tongue. Taste buds relay information to the brain on the nutritional value of food. Recent advances in biochemical and physiological studies have enabled researchers to conclude that bitter taste transduction is mediated by so-called G-protein coupled receptors (GPCRs). GPCRs are 7 transmembrane domain cell surface proteins that amplify signals generated at a cell surface when the receptor interacts with a ligand (a tastant) whereupon they activate heterotrimeric G-proteins. The G-proteins are protein complexes that are composed of alpha and beta-gamma subunits. They are usually referred to by their alpha subunits and classified generally into 4 groups: G alpha s, i, q and 12. The G alpha q type couple with GPCRs to activate phospholipase C which leads to an increase in cellular $Ca^{2+}$. There are many Gq-type G-proteins that are promiscuous and can couple to GPCRs, including taste receptors, and these so-called "promiscuous" G-proteins are well known in the art. These G-proteins dissociate into alpha and beta-gamma subunits upon activation, resulting in a complex cascade of cellular events that results in the cell producing second messengers, such as calcium ions, that enable the cells to send a signal to the brain indicating a bitter response.

There is also anatomical evidence that GPCRs mediate bitter taste transduction: clusters of these receptors are found in mammalian taste cells containing gustducin. Gustducin is a G-protein subunit that is implicated in the perception of bitter taste in mammals see, for example, Chandrashekar, J. et al. (2000) Cell 100: 703-711; Matsunami H. et al. (2000) Nature 404: 601-604; or Adler E. et al. (2000) Cell 100: 693-702. cDNAs encoding such GPCRs have been identified, isolated, and used as templates to compare with DNA libraries using in-silico data-mining techniques to identify other related receptors. In this manner it has been possible to identify a family of related receptors, the so-called T2R or TAS2R family of receptors, that have been putatively assigned as bitter taste receptors.

Humans are able to detect with a limited genetic repertoire of about 30 receptor genes thousands of different bitter compounds. Since their discovery in the year 2000 (Adler E. et al. (2000) supra; Chandrashekar J. et al. (2000) supra; Matsunami H. et al (2000) supra) only few mammalian TAS2Rs have been deorphanised, i.e. ligands, in particular agonists have been identified. The murine mTAS2R5 (Chandrashekar J. et al (2000) supra) and the rat rTAS2R9 (Bufe B. et al. (2002) Nature Genetics 32:397-401) respond to the toxic bitter substance cycloheximide, the mouse mTAS2R8 and the human hTAS2R4 respond to high doses of denatonium and, to a lesser extend, to 6-n-propyl-2-thiouracil (Chandrashekar J. et al. (2000) supra), the human hTAS2R10 and hTAS2R16 respond selectively to strychnine and bitter beta-glucopyranosides, respectively (Bufe B. et al (2002) supra). Although for some TAS2Rs a limited promiscuity (mTAS2R8, hTAS2R4) or specificity for a group of chemically related compounds (hTAS2R16) was reported, the relative selectivity of ligand recognition by the receptors published to date does, by far, not explain the enormous number of bitter tastants recognised by the mammalian gustatory system. Also very little is known about substances that can act as antagonists of bitter taste receptors and thereby reduce or suppress a bitter taste sensation.

The knowledge about compounds that act as bitter receptor antagonists is prerequisite to the implementation of a method to isolate structurally related antagonists which may be at least as potent in suppressing the bitter taste receptor activity as the original antagonist and which may feature additional advantages such as lower toxicity, better solubility, improved stability and so forth. A bitter taste receptor antagonist isolated by such method can also be isolated and modified or combined with other bitter taste receptor antagonists in such a way that it is capable of targeting a broader range of known bitter taste receptors with high affinity to achieve a more effective suppression of bitter taste.

The present invention provides compounds which act as antagonists of human bitter taste receptor hTAS2R38 function. There are two common molecular forms [proline-alanine-valine (PAV) and alanine-valine-isoleucine (AVI)] of the hTAS2R38 bitter taste receptor defined by three nucleotide polymorphisms that result in three amino acid substitutions: Pro49Ala, Ala262Val, and Val296Ile. The ancestral human haplotype at these three amino acids—determined by sequencing DNA from several other ape species, an old world monkey, and a new world monkey—is PAV. This molecular form is common in humans and is associated with tasting; the other common form, the AVI form, is associated with non-tasting of the bitter substance PTC (phenylthiocarbamide) (see Duffy et al. *Alcohol Clin Exp Res.* 2004 November; 28(11): 1629-1637.). The disclosure of the present patent application allows the implementation of a method to isolate additional structurally related antagonists for the bitter taste receptor hTAS2R38 to suppress bitter taste and their use.

DESCRIPTION OF THE INVENTION

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W, Nagel, B. and Klbl, H. eds. (1995), Helvetica Chimica Acta, CH-4010 Basel, Switzerland).

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps. In the following passages different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

In the following definitions of the terms: alkyl, heteroalkyl, cycloalkyl, heterocycloalkyl, alicyclic system, aryl, aralkyl, heteroaryl, heteroaralkyl, alkenyl and alkynyl are provided. These terms will in each instance of its use in the remainder of the specification have the respectively defined meaning and preferred meanings.

The term "alkyl" refers to a saturated straight or branched carbon chain. Preferably, the chain comprises from 1 to 10 carbon atoms, i.e. 1, 2, 3, 4, 5, 6, 7, 8, 9 or 10 e.g. methyl, ethyl methyl, ethyl, propyl, iso-propyl, butyl, iso-butyl, tert-butyl, pentyl, hexyl, heptyl, or octyl. Alkyl groups are optionally substituted.

The term "heteroalkyl" refers to a saturated straight or branched carbon chain. Preferably, the chain comprises from 1 to 9 carbon atoms, i.e. 1, 2, 3, 4, 5, 6, 7, 8, or 9 e.g. methyl, ethyl, propyl, iso-propyl, butyl, iso-butyl, sec-butyl, tert-butyl, pentyl, hexyl, heptyl, octyl, which is interrupted one or more times, e.g. 1, 2, 3, 4, or 5, with the same or different heteroatoms.

Preferably the heteroatoms are selected from O, S, and N, e.g. —O—$CH_3$, —S—$CH_3$, —$CH_2$—O—$CH_3$, —$CH_2$—O—$C_2H_5$, —$CH_2$—S—$CH_3$, —$CH_2$—S—$C_2H_5$, —$C_2H_4$—O—$CH_3$, —$C_2H_4$—O—$C_2H_5$, —$C_2H_4$—S—$CH_3$, —$C_2H_4$—S—$C_2H_5$ etc. Heteroalkyl groups are optionally substituted.

The terms "cycloalkyl" and "heterocycloalkyl", by themselves or in combination with other terms, represent, unless otherwise stated, cyclic versions of "alkyl" and "heteroalkyl", respectively, with preferably 3, 4, 5, 6, 7, 8, 9 or 10 atoms forming a ring, e.g. cyclopropyl, cyclobutyl, cyclopentyl, cyclohexyl, cycloheptyl, cyclooctyl etc. The terms "cycloalkyl" and "heterocycloalkyl" are also meant to include bicyclic, tricyclic and polycyclic versions thereof. If more than one cyclic ring is present such as in bicyclic, tricyclic and polycyclic versions, then these rings may also comprise one or more aryl- or heteroaryl ring. The term "heterocycloalkyl" preferably refers to a saturated ring having five members of which at least one member is a N, O or S atom and which optionally contains one additional O or one additional N; a saturated ring having six members of which at least one member is a N, O or S atom and which optionally contains one additional O or one additional N or two additional N atoms; or a saturated bicyclic ring having nine or ten members of which at least one member is a N, O or S atom and which optionally contains one, two or three additional N atoms. "Cycloalkyl" and "heterocycloalkyl" groups are optionally substituted. Additionally, for heterocycloalkyl, a heteroatom can occupy the position at which the heterocycle is attached to the remainder of the molecule. Preferred examples of cycloalkyl include $C_3$-$C_{10}$-cycloalkyl, in particular cyclopropyl, cyclobutyl, cyclopentyl, cyclohexyl, cycloheptyl, cyclooctyl, cyclononyl, cyclodecyl, spiro[3,3] heptyl, spiro[3,4]octyl, spiro[4,3]octyl, spiro[3,5]nonyl, spiro[5,3]nonyl, spiro[3,6]decyl, spiro[6,3]decyl, spiro[4,5] decyl, spiro[5,4]decyl, bicyclo[4.1.0]heptyl, bicyclo[3.2.0] heptyl, bicyclo[2.2.1]heptyl, bicyclo[2.2.2]octyl, bicyclo [5.1.0]octyl, bicyclo[4.2.0]octyl, octahydro-pentalenyl, octahydro-indenyl, decahydro-azulenyl, adamantly, or decahydro-naphthalenyl. Preferred examples of heterocycloalkyl include $C_3$-$C_{10}$-heterocycloalkyl, in particular 1-(1, 2,5,6-tetrahydropyridyl), 1-piperidinyl, 2-piperidinyl, 3-piperidinyl, 4-morpholinyl, 3-morpholinyl, 1,8 diaza-spiro-[4,5] decyl, 1,7 diaza-spiro-[4,5]decyl, 1,6 diaza-spiro-[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro-[5,4]decyl, 2,7 diaza-spiro [5,4]decyl, 3,8 diaza-spiro[5,4]decyl, 3,7 diaza-spiro[5,4]decyl, 1-aza-7,11-dioxo-spiro[5,5]undecyl, 1,4-diazabicyclo [2.2.2]oct-2-yl, tetrahydrofuran-2-yl, tetrahydrofuran-3-yl, tetrahydrothien-2-yl, tetrahydrothien-3-yl, 1-piperazinyl, or 2-piperazinyl.

The term "alicyclic system" refers to mono, bicyclic, tricyclic or polycyclic version of a cycloalkyl or heterocycloalkyl comprising at least one double and/or triple bond. However, an alicyclic system is not aromatic or heteroaromatic, i.e. does not have a system of conjugated double bonds/free electron pairs. Thus, the number of double and/or triple bonds maximally allowed in an alicyclic system is determined by the number of ring atoms, e.g. in a ring system with up to 5 ring atoms an alicyclic system comprises up to one double bond, in a ring system with 6 ring atoms the alicyclic system comprises up to two double bonds. Accordingly, the "cycloalkenyl" as defined below is a preferred embodiment of an alicyclic ring system. Alicyclic systems are optionally substituted.

The term "aryl" preferably refers to an aromatic monocyclic ring containing 6 carbon atoms, an aromatic bicyclic ring system containing 10 carbon atoms or an aromatic tricyclic ring system containing 14 carbon atoms. Examples are phenyl, naphthyl or anthracenyl. The aryl group is optionally substituted.

The term "aralkyl" refers to an alkyl moiety, which is substituted by aryl, wherein alkyl and aryl have the meaning as outlined above. An example is the benzyl radical. Preferably, in this context the alkyl chain comprises from 1 to 8 carbon atoms, i.e. 1, 2, 3, 4, 5, 6, 7, or 8, e.g. methyl, ethyl methyl, ethyl, propyl, iso-propyl, butyl, iso-butyl, sec-butenyl, tert-butyl, pentyl, hexyl, pentyl, octyl. The aralkyl group is optionally substituted at the alkyl and/or aryl part of the group.

The term "heteroaryl" preferably refers to a five or six-membered aromatic monocyclic ring wherein at least one of the carbon atoms are replaced by 1, 2, 3, or 4 (for the five membered ring) or 1, 2, 3, 4, or 5 (for the six membered ring) of the same or different heteroatoms, preferably selected from O, N and S; an aromatic bicyclic ring system wherein 1, 2, 3, 4, 5, or 6 carbon atoms of the 8, 9, 10, 11 or 12 carbon atoms have been replaced with the same or different heteroatoms, preferably selected from O, N and S; or an aromatic tricyclic ring system wherein 1, 2, 3, 4, 5, or 6 carbon atoms of the 13, 14, 15, or 16 carbon atoms have been replaced with the same or different heteroatoms, preferably selected from O, N and S. Examples are oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothiophenyl, 2-benzothiophenyl, 1H-indazolyl, benzimidazolyl, benzoxazolyl, indoxazinyl, 2,1-benzisoxazoyl, benzothiazolyl, 1,2-benzisothiazolyl, 2,1-benzisothiazolyl, benzotriazolyl, quinolinyl, isoquinolinyl, quinoxalinyl, quinazolinyl, 1,2,3-benzotriazinyl, or 1,2,4-benzotriazinyl.

The term "heteroaralkyl" refers to an alkyl moiety, which is substituted by heteroaryl, wherein alkyl and heteroaryl have the meaning as outlined above. An example is the 2-alkylpyridinyl, 3-alkylpyridinyl, or 2-methylpyridinyl. Preferably, in this context the alkyl chain comprises from 1 to 8 carbon atoms, i.e. 1, 2, 3, 4, 5, 6, 7, or 8, e.g. methyl, ethyl methyl, ethyl, propyl, iso-propyl, butyl, iso-butyl, sec-butenyl, tert-butyl, pentyl, hexyl, pentyl, octyl. The heteroaralkyl group is optionally substituted at the alkyl and/or heteroaryl part of the group.

The terms "alkenyl" and "cycloalkenyl" refer to olefinic unsaturated carbon atoms containing chains or rings with one or more double bonds. Examples are propenyl and cyclohexenyl. Preferably, the alkenyl chain comprises from 2 to 8 carbon atoms, i.e. 2, 3, 4, 5, 6, 7, or 8, e.g. ethenyl, 1-propenyl, 2-propenyl, iso-propenyl, 1-butenyl, 2-butenyl, 3-butenyl, iso-butenyl, sec-butenyl, 1-pentenyl, 2-pentenyl, 3-pentenyl, 4-pentenyl, hexenyl, heptenyl, octenyl. The term also comprises $CH_2$, i.e. methenyl, if the substituent is directly bonded via the double bond. Preferably the cycloalkenyl ring comprises from 3 to 14 carbon atoms, i.e. 3, 4, 5, 6, 7, 8, 9, 10, 11, 12, 13 or 14, e.g. cyclopropenyl, cyclobutenyl, cyclopentenyl, cyclohexenyl, cycloheptenyl, cyclooctyl, cyclononenyl, cyclodecenyl, spiro[3,3]heptenyl, spiro[3,4]octenyl, spiro[4,3]octenyl, spiro[3,5]nonenyl, spiro[5,3]nonenyl, spiro[3,6]decenyl, spiro[6,3]decenyl, spiro[4,5]decenyl, spiro[5,4]decenyl, bicyclo[4.1.0]heptenyl, bicyclo[3.2.0]heptenyl, bicyclo[2.2.1]heptenyl, bicyclo[2.2.2]octenyl, bicyclo[5.1.0]octenyl, bicyclo[4.2.0]octenyl, hexahydro-pentalenyl, hexahydro-indenyl, octahydro-azulenyl, or octahydro-naphthalenyl.

The term "alkynyl" refers to unsaturated carbon atoms containing chains or rings with one or more triple bonds. An example is the propargyl radical. Preferably, the alkynyl chain comprises from 2 to 8 carbon atoms, i.e. 2, 3, 4, 5, 6, 7, or 8, e.g. ethynyl, 1-propynyl, 2-propynyl, 1-butynyl, 2-butynyl, 3-butynyl, 1-pentynyl, 2-pentynyl, 3-pentynyl, 4-pentynyl, hexynyl, pentynyl, or octynyl.

The term "optionally substituted" in each instance if not further specified refers to halogen, $-NO_2$, $-CN$, $-OR'''$, $-NR'R''$, $-COOR'''$, $-CONR'R''$, $-NR'COR''$, $-NR''COR'''$, $-NR'CONR'R''$, $-NR'SO_2E$, $-COR'''$; $-SO_2NR'R''$, $-OOCR'''$, $-CR'''R''''OH$, $-R'''OH$, and $-E$;

R' and R" is each independently selected from the group consisting of hydrogen, alkyl, alkenyl, alkynyl, cycloalkyl, heterocycloalkyl, aryl, heteroaryl, and aralkyl or together form a heteroaryl, or heterocycloalkyl;

R''' and R'''' is each independently selected from the group consisting of hydrogen, alkyl, alkenyl, alkynyl, cycloalkyl, heterocycloalkyl, alkoxy, aryl, aralkyl, heteroaryl, and —NR'R";

E is selected from the group consisting of alkyl, alkenyl, cycloalkyl, alkoxy, alkoxyalkyl, heterocycloalkyl, an alicyclic system, aryl and heteroaryl; optionally substituted.

The present inventors have identified three antagonists, N,N'-diethylthiourea, N,N'-dimethylthiourea and 2-mercaptobenzimidazole which specifically suppress hTAS2R38 human bitter taste receptor (DNA sequence according to SEQ ID NO: 1 and amino acid sequence according to SEQ ID NO: 2) function—an important finding for the food and pharmaceutical industries. The antagonists provided by the present inventors not only enable its use to suppress bitter taste but they also provide the skilled person with a tool to design compound libraries to screen for structurally related antagonists to suppress the bitter response of hTAS2R38 human bitter taste receptor, which in turn enables the development of compounds and compositions to suppress or eliminate bitter tasting components of foods, in particular animal foods, nutrients and dietary supplements and pharmaceutical or homeopathic preparations containing such phytochemicals. Therefore, in one aspect the present invention provides a method for isolating an antagonist of hTAS2R38 bitter taste receptor activity, wherein the bitter taste receptor is encoded by a polynucleotide selected from the group consisting of:

(a) polynucleotide encoding at least the mature form of the polypeptide having the amino acid sequence as shown in SEQ ID NO: 2;

(b) polynucleotide having the coding nucleotide sequence as shown in SEQ ID NO: 1 encoding at least the mature form of the polypeptide;

(c) polynucleotide encoding a fragment or derivative of a polypeptide encoded by a polynucleotide of any one of (a) to (b), wherein in said derivative one or more amino acid residues are conservatively substituted compared to said polypeptide, and said fragment or derivative has hTAS2R38 bitter taste receptor activity;

(d) polynucleotide which is an ortholog of the polynucleotide sequences shown in SEQ ID NO: 1 encoding at least the mature form of the corresponding bitter taste receptor;

(e) polynucleotide which encodes a polypeptide having hTAS2R38 bitter taste receptor activity, and where said polypeptide is at least 80% identical to a polypeptide as shown in SEQ ID NO: 2;

comprising the steps:

(1) contacting a bitter taste receptor encoded by said polynucleotide or a host cell genetically engineered with said polynucleotide or with a vector containing said polynucleotide to express said bitter taste receptor with a potential antagonist or a pharmaceutically acceptable salt thereof having a structure according to formula (I) or is a tautomer thereof:

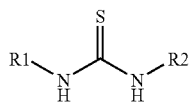

(I)

wherein;
R¹ is selected from the group consisting of alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_1$-$C_6$ alkenyl, e.g. $C_1$, $C_2$, $C_3$, $C_4$, $C_5$, or $C_6$ alkenyl, preferably methenyl, ethenyl, 1-propenyl, 2-propenyl, 1-iso-propenyl, 2-iso-propenyl, 1-butenyl, 2-butenyl, 3-butenyl; alkynyl, in particular $C_2$-$C_6$ alkynyl, e.g. $C_2$, $C_3$, $C_4$, $C_5$, or $C_6$ alkynyl; cycloalkyl, e.g. $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo [2.2.1]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantly, decahydro-naphthalenyl, 2-methylene-decahydro-naphthalenyl, or 2-methylene-decahydro-naphthalen-1-yl; alkoxy, in particular $C_1$-$C_6$ alkoxy, e.g. $C_1$, $C_2$, $C_3$, $C_4$, $C_5$, or $C_6$ alkoxy, preferably methoxy, ethoxy, propoxy, iso-propoxy, butoxy, iso-butoxy, tert-butoxy, pentoxy, or hexoxy; alkoxyalkyl, in particular $C_1$-$C_6$ alkoxy-$C_1$-$C_6$ alkyl, e.g. methoxymethyl, ethoxymethyl, propoxymethyl, methoxyethyl, ethoxyethyl, propoxyethyl, methoxypropyl, ethoxypropyl, or propoxypropyl; heterocycloalkyl, e.g. $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexanyl, 1,8 diaza-spiro-[4,5]decyl, 1,7 diaza-spiro-[4,5]decyl, 1,6 diaza-spiro-[4,5]decyl, 2,8 diaza-spiro [4,5]decyl, 2,7 diaza-spiro[4,5]decyl, 2,6 diaza-spiro [4,5]decyl, 1,8 diaza-spiro-[5,4]decyl, 1,7 diaza-spiro-[5,4]decyl, 2,8 diaza-spiro-[5,4]decyl, 2,7 diaza-spiro[5,4]decyl, 3,8 diaza-spiro[5,4]decyl, 3,7 diaza-spiro[5,4]decyl, 1-aza-7,11-dioxo-spiro[5,5] undecyl, 1,4-diazabicyclo[2.2.2]oct-2-yl, tetrahydrofuran-2-yl, tetrahydrofuran-3-yl, tetrahydrothien-2-yl, tetrahydrothien-3-yl, piperazinyl, decahydroquinolinyl, decahydro-isoquinolinyl, decahydro-quinoxalinyl, or decahydro-quinazolinyl; an alicyclic system, which may comprise one or more heteroatoms preferably selected from the group consisting of O, S, or N; in particular 1,2-dihydropyridinyl, 1,2,5,6-tetrahydropyridinyl, 1,2,3,4-tetrahydropyridyl, 1,2-dihydropyrazyl, 1,2,3,4-tetrahydropyrazyl, cyclopropenyl, cyclobutenyl, cyclopentenyl, cyclohexenyl, cycloheptenyl; aryl, in particular phenyl, naphthalenyl or anthracenyl; or heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; optionally substituted;

R² is selected from the group consisting of alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_1$-$C_6$ alkenyl, e.g. $C_1$, $C_2$, $C_3$, $C_4$, $C_5$, or $C_6$ alkenyl, preferably methenyl, ethenyl, 1-propenyl, 2-propenyl, 1-iso-propenyl, 2-iso-propenyl, 1-butenyl, 2-butenyl, 3-butenyl; alkynyl, in particular $C_2$-$C_6$ alkynyl, e.g. $C_2$, $C_3$, $C_4$, $C_5$, or $C_6$ alkynyl; cycloalkyl, e.g. $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo [2.2.1]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantly, decahydro-naphthalenyl, 2-methylene-decahydro-naphthalenyl, or 2-methylene-decahydro-naphthalen-1-yl; alkoxy, in particular $C_1$-$C_6$ alkoxy, e.g. $C_1$, $C_2$, $C_3$, $C_4$, $C_5$, or $C_6$ alkoxy, preferably methoxy, ethoxy, propoxy, iso-propoxy, butoxy, iso-butoxy, tert-butoxy, pentoxy, or hexoxy; alkoxyalkyl, in particular $C_1$-$C_6$ alkoxy-$C_1$-$C_6$ alkyl, e.g. methoxymethyl, ethoxymethyl, propoxymethyl, methoxyethyl, ethoxyethyl, propoxyethyl, methoxypropyl, ethoxypropyl, or propoxypropyl; heterocycloalkyl, e.g. $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexanyl, 1,8 diaza-spiro-[4,5]decyl, 1,7 diaza-spiro-[4,5]decyl, 1,6 diaza-spiro-[4,5]decyl, 2,8 diaza-spiro [4,5]decyl, 2,7 diaza-spiro[4,5]decyl, 2,6 diaza-spiro [4,5]decyl, 1,8 diaza-spiro-[5,4]decyl, 1,7 diaza-spiro-[5,4]decyl, 2,8 diaza-spiro-[5,4]decyl, 2,7 diaza-spiro[5,4]decyl, 3,8 diaza-spiro[5,4]decyl, 3,7 diaza-spiro[5,4]decyl, 1-aza-7,11-dioxo-spiro[5,5] undecyl, 1,4-diazabicyclo[2.2.2]oct-2-yl, tetrahydrofuran-2-yl, tetrahydrofuran-3-yl, tetrahydrothien-2-yl, tetrahydrothien-3-yl, piperazinyl, decahydroquinolinyl, decahydro-isoquinolinyl, decahydro-quinoxalinyl, or decahydro-quinazolinyl; an alicyclic system, which may comprise one or more heteroatoms preferably selected from the group consisting of O, S, or N; in particular 1,2-dihydropyridinyl, 1,2,5,6-tetrahydropyridinyl, 1,2,3,4-tetrahydropyridyl, 1,2-dihydropyrazyl, 1,2,3,4-tetrahydropyrazyl, cyclopropenyl, cyclobutenyl, cyclopentenyl, cyclohexenyl, cycloheptenyl; aryl, in particular phenyl, naphthalenyl or anthracenyl; or heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; optionally substituted or $R^1$ and $R^2$ together form a heterocycloalkyl, e.g. $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular, imidazolidinyl, 1,3-diazacyclohexanyl, 1,3-diazacycloheptanyl, or decahydro-quinazolinyl; an alicyclic system comprising two nitrogen atoms indicated in formula (I) and which may comprise one or more further heteroatoms preferably selected from the group consisting of O, S, or N; in particular dihydroimidazolyl, e.g. 1,2-dihydro-imidazolyl, dihydro-pyrimidinyl, e.g. 4,5, dihydro-pyrimidinyl, 1,2-dihydro-pyrimidinyl, 2,3-dihydro-1H-benzoimidazolyl, 2,3-dihydro-1H-imidazo[4,5-c]pyridinyl, 2,3-dihydro-1H-imidazo[4,5-d]pyridinyl, or 6,7-dihydro-5H-imidazo[4,5-c]pyridazinyl; or heteroaryl, in particular imidazolyl, 1,2,4-triazolyl, pyrimidinyl, 1,2,4-triazinyl, 1,3,5-triazinyl, benzimidazolyl, quinazolinyl, 1,2,4-benzotriazinyl, 3H-imidazo[4,5-b]pyridinyl, 3H-imidazo[4,5-c]pyridinyl, 1H-imidazo[4,5-b]pyrazinyl, 7H-purine, or 7H-Imidazo[4,5-c]pyridazinyl;

(2) determining whether the potential antagonist inhibits the bitter taste receptor activity;

(3) isolating a potential antagonist that reduces the activity of hTAS2R38 stimulated by an agonist of hTAS2R38 or a structurally related agonist, preferably by at least by 10% preferably at the same molar concentration;

wherein prior, concomitantly and/or after step (1) said bitter taste receptor or said host cell is contacted with an agonist of bitter taste receptor hTAS2R38 or a structurally related agonist thereof. In above indicated formula (I) two additional tautomeric forms, i.e. isothiourea forms, are possible wherein the double bond is located between the carbon atom and either of the nitrogen atoms. These tautomeric forms are also comprised by the present invention. Whether a given compound will primarily be present in the thiourea or isothiourea form will depend on the groups flanking the respective nitrogen atom.

In a preferred embodiment the residues $R^1$ and $R^2$ are identical to each other.

In a further preferred embodiment both $R^1$ and $R^2$ are hydrophobic.

The polynucleotide employed in both aspects of the present invention encodes a polypeptide that still exhibits essentially the same activity as the mature hTAS2R38 bitter taste receptor, respectively, i.e. has "bitter taste receptor activity". Preferably the polypeptide has at least 20% (e.g., at least: 20%; 30%; 40%; 50%; 60%; 70%; 80%; 90%; 95%; 98%; 99%; 99.5%; or 100% or even more) of the activity of the full-length mature hTAS2R38. One preferred way of measuring hTAS2R38 activity, is the ability to release intracellular calcium in a heterologous cell expression system like, for example, (HEK293T/G16gust44) cells that stably expresses a chimeric G-protein consisting of Gα16 and 44 carboxylterminal amino acids of α-gustducin, in response to bitter tastants, which is dependent on the expression of polypeptides encoded by the polynucleotides of the present invention.

The amount of intracellular calcium released can be monitored by, for example, the in vitro FLIPR assay described herein but also by the measurement of one of a variety of other parameters including, for example, $IP_3$ or cAMP. Additional ways of measuring G-protein coupled receptor activity are known in the art and comprise without limitation electrophysiological methods, transcription assays, which measure, e.g. activation or repression of reporter genes which are coupled to regulatory sequences regulated via the respective G-protein coupled signalling pathway, such reporter proteins comprise, e.g., CAT or LUC; assays measuring internalization of the receptor; or assays in frog melanophore systems, in which pigment movement in melanophores is used as a readout for the activity of adenylate cyclase or phospholipase C (PLC), which in turn are coupled via G-proteins to exogenously expressed receptors (see, for example, McClintock T. S. et al. (1993) Anal. Biochem. 209: 298-305; McClintock T. S. and Lerner M. R. (1997) Brain Res. Brain, Res. Protoc. 2: 59-68, Potenza M N (1992) Pigment Cell Res. 5: 372-328, and Potenza M. N. (1992) Anal. Biochem. 206: 315-322).

The term "potential antagonist", comprises any perceivable chemical substance or combination thereof having a structure according to formula (I) in a non-purified, partially purified or purified state. The potential antagonist is selected on the basis of its antagonizing behaviour. An "isolated antagonist" of hTAS2R38 bitter taste receptor activity, respectively, is a substance which reduces the activity of hTAS2R38 stimulated by the hTAS2R38 bitter taste receptor agonist, preferably selected from the group consisting of the agonists (bitter substances) acethylthiourea, N,N-dimethylthioformamide, N,N'-diphenylthiourea, N,N'-ethylene-thiourea, N-ethylthiourea, methimazol, 4(6)-methyl-2-thiouracil, N-methylthiourea, phenylthiocarbamide (PTC), 6-phenyl-2-thiouracil, 5-propyl-2-thiouracil, 6-propyl-2-thiouracil (PROP), tetramethyl thiourea, thioacetamide, thioacetanilid, and 2-thiobarbituric acid and structurally related agonists thereof. Preferably this reduction is by at least 10% (e.g., at least: 10%, 15%; 20%; 30%; 40%; 50%; 60%; 70%; 80%; 90%; 95%; 98%; 99%; 99.5%; or 100%), preferably at the same molar concentration. The extend of the lowering of the hTAS2R38 bitter taste receptor activity, caused by the antagonist is determined in the presence of said agonist, e.g. one of the compounds indicated above or a structurally related compound, which may be added prior, concomitantly or after addition of the antagonist. Preferably, the identified antagonist exerts this inhibitory activity, if present in the same molar, 2-fold, 5-fold, 10-fold. 50-fold or 100-fold molar concentration as the agonist. In a preferred embodiment, the "potential antagonist" is a compound structurally related to N,N'-diethylthiourea, N,N'-dimethylthiourea or 2-mercaptobenzimidazole.

In a preferred embodiment, the potential bitter taste receptor hTAS2R38 antagonist is used in the method of the invention has a different structure than any of the preferred bitter taste receptor hTAS2R38 agonists (bitter substances) listed above, i.e. acethylthiourea, N,N-dimethylthioformamide, N,N'-diphenylthiourea, N,N'-ethylene-thiourea, N-ethylthiourea, methimazol, 4(6)-methyl-2-thiouracil, N-methylthiourea, phenylthiocarbamide (PTC), 6-phenyl-2-thiouracil, 5-propyl-2-thiouracil, 6-propyl-2-thiouracil (PROP) tetramethyl thiourea, thioacetamide, thioacetanilid, and 2-thiobarbituric acid.

Preferably, the antagonist exerts its antagonizing action when it is contacted prior, concomitantly or after, preferably concomitantly, to contacting the hTAS2R38 polypeptide, the host cell genetically engineered with a polynucleotide encoding hTAS2R38 polypeptide as defined above or a vector containing a polynucleotide as defined above to express hTAS2R38 polypeptide with said hTAS2R38 agonist. Preferably, if contacted at the same molar concentration as said hTAS2R38 agonist.

The term "potential antagonist", preferably comprises substances structurally related to the antagonists N,N'-diethylthiourea, N,N'-dimethylthiourea, or 2-mercaptobenzimidazole a in a non-purified, partially purified or purified state.

The hTAS2R38 polynucleotide molecule, usable in the method of the present invention can be DNA, cDNA, genomic DNA, synthetic DNA, or RNA, and can be double-stranded or single-stranded, the sense and/or an antisense strand. Segments of these molecules are also considered within the scope of the invention, and can be produced by, for example, the polymerase chain reaction (PCR) or generated by treatment with one or more restriction endonucleases. A ribonucleic acid (RNA) molecule can be produced by in vitro transcription.

The polynucleotide molecules usable in the method of the present invention can contain naturally occurring sequences, or sequences that differ from those that occur naturally, but, due to the degeneracy of the genetic code, encode the same polypeptide (for example, the polypeptide with SEQ ID NO: 2). In addition, these nucleic acid molecules are not limited to coding sequences, e.g., they can include some or all of the non-coding sequences that lie upstream or downstream from a coding sequence.

The polynucleotide molecules of the invention can be synthesized in vitro (for example, by phosphoramidite-based synthesis) or obtained from a cell, such as the cell of a bacteria or a mammal. The nucleic acids can be those of a human but also include orthologous polynucleotides derived from a non-human primate, mouse, rat, guinea pig, cow, sheep, horse, pig, rabbit, dog, or cat as long as they fulfill the criteria set out above. Combinations or modifications of the polynucleotides within these types of nucleic acids are also encompassed. Means to identify orthologous polynucleotide molecules of the invention are available to a person of skill and comprise the use of BLAST searches (see below) and database mining of databases such as the EMBL, NCBI and other databases comprising polynucleotides and amino acid sequences.

In addition, the polynucleotides usable in the method of the present invention can encompass segments that are not found as such in the natural state. Thus, the invention encompasses recombinant nucleic acid molecules incorporated into a vector (for example, a plasmid or viral vector) or into the genome of a heterologous cell (or the genome of a homologous cell, at a position other than the natural chromosomal location). Recombinant nucleic acid molecules and uses therefore are discussed further below.

In certain preferred embodiments the method of the present invention uses isolated nucleic acid molecules which are at least 50% (or 55%, 60%, 65%, 70%, 75%, 80%, 85%, 90%, 95%, or 98%) identical to: (a) a nucleic acid molecule that encodes the polypeptide of SEQ ID NO: 2; (b) the polynucleotide sequence of SEQ ID NO: 1 and (c) a nucleic acid molecule which includes a segment of at least 30 (e.g., at least 30, 40, 50, 60, 80, 100, 125, 150, 175, 200, 250, 300, 400, 500, 600, 700, 800, 850, and 900) contiguous polynucleotides of SEQ ID NO: 1, in as long as these nucleic acid molecules encode a polypeptide having hTAS2R38 bitter taste receptor activity.

The determination of percent identity between two sequences is accomplished using the mathematical algorithm of Karlin and Altschul (1993) Proc. Natl. Acad. ScI USA 90: 5873-5877. Such an algorithm is incorporated into the BLASTN and BLASTP programs of Altschul et al. (1990) J. MoI. Biol. 215: 403-410. BLAST polynucleotide searches are performed with the BLASTN program, score=100, word length=12, to obtain polynucleotide sequences homologous to hTAS2R38 encoding nucleic acids. BLAST protein searches are performed with the BLASTP program, score=50, wordlength=3, to obtain amino acid sequences homologous to the hTAS2R38 polypeptide, respectively. To obtain gapped alignments for comparative purposes, Gapped BLAST is utilized as described in Altschul et al. (1997) Nucleic Acids Res. 25: 3389-3402. When utilizing BLAST and Gapped BLAST programs, the default parameters of the respective programs are used.

Hybridization can also be used as a measure of homology between two nucleic acid sequences. A nucleic acid sequence encoding hTAS2R38, or a portion thereof, can be used as a hybridization probe according to standard hybridization techniques. The hybridization of a hTAS2R38 probe to DNA or RNA from a test source (e.g., a mammalian cell) is an indication of the presence of the hTAS2R38 DNA or RNA in the test source. Hybridization conditions are known to those skilled in the art and can be found, for example, in Current Protocols in Molecular Biology, John Wiley & Sons, N. Y., 6.3.1-6.3.6, 1991. Moderate hybridization conditions are defined as equivalent to hybridization in 2× sodium chloride/sodium citrate (SSC) at 30C, followed by a wash in 1×SSC, 0.1% SDS at 50° C. Highly stringent conditions are defined as equivalent to hybridization in 6× sodium chloride/sodium citrate (SSC) at 45° C., followed by a wash in 0.2×SSC, 0.1% SDS at 65° C.

The polynucleotides or proteins usable in the method of the present invention can be comprised in a vector containing the polynucleotide(s) or a protein encoded by above-mentioned polynucleotide. The term "vector" refers to a protein or a polynucleotide or a mixture thereof which is capable of being introduced or of introducing the proteins and/or nucleic acid comprised therein into a cell. It is preferred that the proteins encoded by the introduced polynucleotide are expressed within the cell upon introduction of the vector.

In a preferred embodiment a vector usable in the method of the present invention comprises plasmids, phagemids, phages, cosmids, artificial mammalian chromosomes, knock-out or knock-in constructs, viruses, in particular adenoviruses, vaccinia viruses, attenuated vaccinia viruses, canary pox viruses, lentivirus (Chang, L J. and Gay, E. E. (2001) Curr. Gene Therap. 1: 237-251), herpes viruses, in particular Herpes simplex virus (HSV-I, Carlezon, W. A. et al. (2000) Crit. Rev. Neurobiol. 14: 47-67), baculovirus, retrovirus, adeno-associated-virus (AAV, Carter, P J. and Samulski, R J. (2000) J. MoI. Med. 6:17-27), rhinovirus, human immune deficiency virus (HIV), filovirus and engineered versions thereof (see, for example, Cobinger G. P. et al. (2001) Nat. Biotechnol. 19:225-30), virosomes, "naked" DNA liposomes, and nucleic acid coated particles, in particular gold spheres. Particularly preferred are viral vectors like adenoviral vectors or retroviral vectors (Lindemann et al. (1997) MoI. Med. 3: 466-76 and Springer et al. (1998) MoI. Cell. 2: 549-58). Liposomes are usually small unilamellar or multilamellar vesicles made of cationic, neutral and/or anionic lipids, for example, by ultrasound treatment of liposomal suspensions. The DNA can, for example, be ionically bound to the surface of the liposomes or internally enclosed in the liposome. Suitable lipid mixtures are known in the art and comprise, for example, DOTMA (1,2-Dioleyloxpropyl-3-trimethylammoniumbromid) and DOPE (Dioleoyl-phosphatidylethanolamin) which both have been used on a variety of cell lines.

Nucleic acid coated particles are another means for the introduction of nucleic acids into cells using so called "gene guns", which allow the mechanical introduction of particles into cells. Preferably the particles itself are inert, and therefore, are in a preferred embodiment made out of gold spheres.

In a further aspect polynucleotides usable in the method of the present invention are operatively linked to expression control sequences allowing expression in prokaryotic and/or eukaryotic host cells. The transcriptional/translational regulatory elements referred to above include but are not limited to inducible and non-inducible, constitutive, cell cycle regulated, metabolically regulated promoters, enhancers, operators, silencers, repressors and other elements that are known to those skilled in the art and that drive or otherwise regulate gene expression. Such regulatory elements include but are not limited to regulatory elements directing constitutive expression like, for example, promoters transcribed by RNA polymerase III like, e.g. promoters for the snRNA U6 or scRNA 7SK gene, the cytomegalovirus hCMV immediate early gene, the early or late promoters of SV40 adenovirus, viral promoter and activator sequences derived from, e.g. NBV, HCV, HSV, HPV, EBV, HTLV, MMTV or HIV; which allow inducible expression like, for example, CUP-I promoter, the tet-repressor as employed, for example, in the tet-on or tet-off systems, the lac system, the trp, system; regulatory elements directing tissue specific expression, preferably taste bud specific expression, e.g. PLCβ2 promoter or gustducin promoter, regulatory elements directing cell cycle specific expression like, for example, cdc2, cdc25C or cyclin A; or the TAC system, the TRC system, the major operator and promoter regions of phage A, the control regions of fd coat protein, the promoter for 3-phosphoglycerate kinase, the promoters of acid phosphatase, and the promoters of the yeast α- or a-mating factors.

As used herein, "genetically engineered" means that the host cell is transgenic for the polynucleotide or vector containing the polynucleotide.

A polypeptide encoding a "mature form" of a protein or polypeptide means that said protein or polypeptide contains all polypeptide elements that allow it to undergo some or all potential post- or cotranslational processes such as proteolytic processing, phosphorylation, lipidation and the like comprised in the state of the art such that said polypeptide or protein can correctly fold and carry out part or all of its wild type function once it reaches its "mature form".

As used herein, "operatively linked" means incorporated into a genetic construct so that expression control sequences effectively control expression of a coding sequence of interest.

Similarly, the polynucleotides usable in the method of the present invention can form part of a hybrid gene encoding additional polypeptide sequences, for example, a sequence that functions as a marker or reporter. Examples of marker and reporter genes include β-lactamase, chloramphenicol acetyltransferase (CAT), adenosine deaminase (ADA), aminoglycoside phosphotransferase (neo$^r$, G418$^r$), dihydrofolate reductase (DHFR), hygromycin-B-phosphotransferase (HPH), thymidine kinase (TK), lacZ (encoding β-galactosidase), and xanthine guanine phosphoribosyl-transferase (XGPRT). As with many of the standard procedures associated with the practice of the method of the invention, skilled artisans will be aware of additional useful reagents, for example, additional sequences that can serve the function of a marker or reporter.

The method of the present invention may also use hybrid polypeptides or polynucleotides encoding them. In general a hybrid polypeptide will include a first portion and a second portion; the first portion being one or more hTAS2R38 polypeptide and the second portion being, for example, the reporter(s) described above or an Ig constant region or part of an Ig constant region, e.g., the CH2 and CH3 domains of IgG2a heavy chain. Other hybrids could include an antigenic tag or His tag to facilitate purification and/or detection. Recombinant nucleic acid molecules can also contain a polynucleotide sequence encoding the hTAS2R38, polypeptide operatively linked to a heterologous signal sequence. Such signal sequences can direct the protein to different compartments within the cell and are well known to someone of skill in the art. A preferred signal sequence is a sequence that facilitates secretion of the resulting protein.

Another aspect of the present invention is the use of a host cell genetically engineered with a polynucleotide or a vector as outlined above. The host cells that may be used in the method of the present invention include but are not limited to prokaryotic cells such as bacteria (for example, *E. coli* and *B. subtilis*), which can be transformed with, for example, recombinant bacteriophage DNA, plasmid DNA, or cosmid DNA expression vectors containing the polynucleotide molecules of the invention; simple eukaryotic cells like yeast (for example, *Saccharomyces* and *Pichia*), which can be transformed with, for example, recombinant yeast expression vectors containing the polynucleotide molecule of the invention; insect cell systems like, for example, Sf9 or Hi5 cells, which can be infected with, for example, recombinant virus expression vectors (for example, baculovirus) containing the polynucleotide molecules; amphibian cells, e.g. *Xenopus oocytes*, which can be injected with, for example, plasmids; plant cell systems, which can be infected with, for example, recombinant virus expression vectors (for example, cauliflower mosaic virus (CaMV) or tobacco mosaic virus (TMV)) or transformed with recombinant plasmid expression vectors (for example, Ti plasmid) containing a hTAS2R38, polynucleotide sequence; or mammalian cell systems (for example, COS, CHO, BHK, HEK293, VERO, HeLa, MDCK, Wi38, and NIH 3T3 cells), which can be transformed with recombinant expression constructs containing, for example, promoters derived, for example, from the genome of mammalian cells (for example, the metallothionein promoter) from mammalian viruses (for example, the adenovirus late promoter and the vaccinia virus 7.5K promoter) or from bacterial cells (for example, the tet-repressor binding is employed in the tet-on and tet-off systems). Also useful as host cells are primary or secondary cells obtained directly from a mammal and transfected with a plasmid vector or infected with a viral vector. Depending on the host cell and the respective vector used to introduce the polynucleotide of the invention the polynucleotide can integrate, for example, into the chromosome or the mitochondrial DNA or can be maintained extrachromosomally like, for example, episomally or can be only transiently comprised in the cells.

In a preferred embodiment, the hTAS2R38 receptor, expressed by such cells is functional and has bitter taste receptor activity, i.e., upon binding to one or more bitter molecules it triggers an activation pathway in the cell. The cells are preferably mammalian (e.g., human, non-human primate, horse, bovine, sheep, pig, dog, cat, goat, rabbit, mouse, rat, guinea pig, hamster, or gerbil) cells, insect cells, bacterial cells, or fungal (including yeast) cells. The polypeptides usable in the method of the invention include all those disclosed herein and functional fragments of these polypeptides. The terms "polypeptide" and "protein" are used interchangeably and mean any peptide-linked chain of amino acids, regardless of length or post-translational modification. As used herein, a functional fragment of the hTAS2R38 bitter taste receptor is a fragment of the hTAS2R38 bitter taste receptor, that is shorter than the full-length hTAS2R38 bitter taste receptor polypeptide, but that has at least 20% (e.g., at least: 20%, 30%, 40%, 50%, 60%, 70%, 80%, 90%, 95%, 98%, 99%, 99.5%, 100%, 150%, 200%, 500%, 1000%, 10000% or even more) of the ability of the full-length hTAS2R38 to be stimulated by bitter substances such as e.g. the bitter receptor agonists described herein. Binding assays and bitter substances for hTAS2R38 are described above and below. The polypeptides can also include fusion proteins that contain either a full-length hTAS2R38 polypeptide or a functional fragment of it fused to an unrelated amino acid sequence. The unrelated sequences can add further functional domains or signal peptides.

The polypeptides can be any of those described above but with not more than 50 (e.g., not more than: 50, 45, 40, 35, 30, 25, 20, 15, 14, 13, 12, 11, 10, nine, eight, seven, six, five, four, three, two, or one) conservative substitutions. Conservative substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine. All that is required of a polypeptide having one or more conservative substitutions is that it has at least 20% (e.g., at least: 20%; 30%; 40%; 50%; 60%; 70%; 80%; 90%; 95%; 98%; 99%; 99.5%; 100%, 150%, 200%, 500%, 1000%, 10000% or even more) of the ability of the full-length hTAS2R38 to be stimulated by a hTAS2R38 agonist.

Polypeptides and fragments of the polypeptides useable in the method of the present invention can be modified, for example, for in vivo use by the addition of blocking agents, at the amino- and/or carboxyl-terminal ends, to facilitate survival of the relevant polypeptide in vivo. This can be useful in those situations in which the peptide termini tend to be degraded by proteases prior to cellular uptake. Such blocking agents can include, without limitation, additional related or unrelated peptide sequences that can be attached to the amino and/or carboxyl terminal residues of the peptide to be administered. This can be done either chemically during the synthesis of the peptide or by recombinant DNA technology by methods familiar to artisans of average skill. The antagonists or agonists of the bitter taste receptors identified herein are of great importance for specific stimulation of a given bitter taste receptor and identification of substances that antagonize it, respectively.

The term "contacting" in the context of the present invention means any interaction between the antagonist and/or agonist with the polypeptide or the host cell, whereby any of the at least two components can be independently of each other in a liquid phase, for example in solution, or in suspension or can be bound to a solid phase, for example, in the form of an essentially planar surface or in the form of particles, beads or the like, in a preferred embodiment a multitude of different compounds are immobilized on a solid surface like, for example, on a compound library chip and the protein of the present invention is subsequently contacted with such a chip, in another preferred embodiment the host cells are genetically engineered with a polynucleotide encoding hTAS2R38, or with a vector containing such a polynucleotide, express the hTAS2R38 bitter taste receptor at the cell surface and are contacted separately in small containers, e. g., micro-titre plates, with various compounds.

As used herein, the term "isolating" an antagonist refers to the process of selecting, identifying, isolating or evolving an antagonist out of a group of at least two different potential antagonists whereby the said selected, identified, isolated or evolved antagonist exhibits preferred features compared with the other antagonists such as, for example, stronger and/or longer or shorter inhibition of receptor activation.

The present invention also features a method for the production of a modified antagonist of hTAS2R38, wherein an antagonist identified in a method of the invention or N,N'-diethylthiourea, N,N'-dimethylthiourea or 2-mercaptobenzimidazole is modified by the addition and/or exchange of at least one substituent. It is preferred that such modified antagonist is further selected based on that it reduces the activity of hTAS2R38 stimulated by an agonist of hTAS2R38 or a structurally related agonist at least as good as the identified antagonist, N,N'-diethylthiourea, N,N'-dimethylthiourea or 2-mercaptobenzimidazole at the same molar concentration.

From the examples disclosed herein, a person of skill will realize that the hTAS2R38 antagonists N,N'-dimethylthiourea and 2-mercaptobenzimidazole can act as agonists for human bitter taste receptor hTAS2R38 when used at low concentrations. Specifically, N,N'-dimethylthiourea and 2-mercaptobenzimidazole act as agonist of human bitter taste receptor hTAS2R38 at concentrations of below 3 mM and below 0.01 mM, respectively. Therefore, when selecting a modified antagonist as stated above, it is further preferred that above stated methods are carried out wherein the concentration of N,N'-dimethylthiourea is larger than 3 mM, 4 mM, 5 mM, 10 mM, 50 mM or larger than 100 mM and the concentration of 2-mercaptobenzimidazole is larger than 0.01 mM, 0.02 mM, 0.05 mM, 0.1 mM, 0.2 mM or larger than 0.5 mM.

As a further step after measuring the antagonizing effect of a potential antagonist and after having measured the decrease of bitter taste for at least two different potential antagonists at least one potential antagonist can be selected, for example, on grounds of the detected decrease of intracellular release of calcium.

In a preferred embodiment of the method of the present invention the potential antagonist that is employed in the identification process has a structure according to formula (II) or formula (III) or is a tautomer thereof:

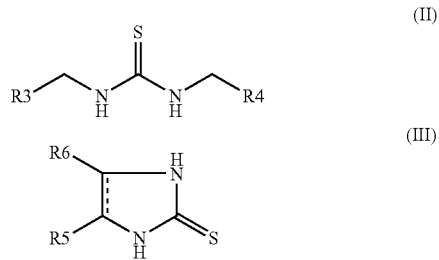

wherein $R^3$ is selected from the group consisting of hydrogen; halogen, in particular F, Cl, Br or I; —$NO_2$; —CN; alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_1$-$C_6$ alkenyl, e.g. $C_1$, $C_2$, $C_3$, $C_4$, $C_5$, or $C_6$ alkenyl, preferably methenyl, ethenyl, 1-propenyl, 2-propenyl, 1-iso-propenyl, 2-iso-propenyl, 1-butenyl, 2-butenyl, 3-butenyl; alkynyl, in particular $C_2$-$C_6$ alkynyl, e.g. $C_2$, $C_3$, $C_4$, $C_5$, or $C_6$ alkynyl; cycloalkyl, e.g. $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantly, decahydro-naphthalenyl, 2-methylene-decahydro-naphthalenyl, or 2-methylene-decahydro-naphthalen-1-yl; alkoxy, in particular $C_1$-$C_6$ alkoxy, e.g. $C_1$, $C_2$, $C_3$, $C_4$, $C_5$, or $C_6$ alkoxy, preferably methoxy, ethoxy, propoxy, iso-propoxy, butoxy, iso-butoxy, tert-butoxy, pentoxy, or hexoxy; alkoxyalkyl, in particular $C_1$-$C_6$ alkoxy-$C_1$-$C_6$ alkyl, e.g. methoxymethyl, ethoxymethyl, propoxymethyl, methoxyethyl, ethoxyethyl, propoxyethyl, methoxypropyl, ethoxypropyl, or propoxypropyl; heterocycloalkyl, e.g. $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexanyl, 1,8 diaza-spiro-[4,5]decyl, 1,7 diaza-spiro-[4,5]decyl, 1,6 diaza-spiro-[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro[5,4]decyl, 2,7 diaza-spiro[5,4]decyl, 3,8 diaza-spiro[5,4]decyl, 3,7 diaza-spiro[5,4]decyl, 1-aza-7,11-dioxo-spiro[5,5]undecyl, 1,4-diazabicyclo[2.2.2]oct-2-yl, tetrahydrofuran-2-yl, tetrahydrofuran-3-yl, tetrahydrothien-2-yl, tetrahydrothien-3-yl, piperazinyl, decahydroquinolinyl, decahydro-isoquinolinyl, decahydro-quinoxalinyl, or decahydro-quinazolinyl; an alicyclic system, which may comprise one or more heteroatoms preferably selected from the group consisting of O, S, or N; in particular 1,2-dihydropyridinyl, 1,2,5,6-tetrahydropyridinyl, 1,2,3,4-tetrahydropyridyl, 1,2-dihydropyrazyl, 1,2,3,4-tetrahydropyrazyl, cyclopropenyl, cyclobutenyl, cyclopentenyl, cyclohexenyl, cycloheptenyl; aryl, in particular phenyl, naphthalenyl or anthracenyl; or heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; optionally substituted; preferably hydrogen, alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; optionally substituted;

$R^4$ is selected from the group consisting of hydrogen; halogen, in particular F, Cl, Br or I; —$NO_2$; —CN; alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_1$-$C_6$ alkenyl, e.g. $C_1$, $C_2$, $C_3$, $C_4$, $C_5$, or $C_6$ alkenyl, preferably methenyl, ethenyl, 1-propenyl, 2-propenyl, 1-iso-propenyl, 2-iso-propenyl, 1-butenyl, 2-butenyl, 3-butenyl; alkynyl, in particular $C_2$-$C_6$ alkynyl, e.g. $C_2$, $C_3$, $C_4$, $C_5$, or $C_6$ alkynyl; cycloalkyl, e.g. $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantly, decahydro-naphthalenyl, 2-methylene-decahydro-naphthalenyl, or 2-methylene-decahydro-naphthalen-1-yl; alkoxy, in particular $C_1$-$C_6$ alkoxy, e.g. $C_1$, $C_2$, $C_3$, $C_4$, $C_5$, or $C_6$ alkoxy, preferably methoxy, ethoxy, propoxy, iso-propoxy, butoxy, iso-butoxy, tert-butoxy, pentoxy, or hexoxy; alkoxyalkyl, in particular $C_1$-$C_6$ alkoxy-$C_1$-$C_6$ alkyl, e.g. methoxymethyl, ethoxymethyl, propoxymethyl, methoxyethyl, ethoxyethyl, propoxyethyl, methoxypropyl, ethoxypropyl, or propoxypropyl; heterocycloalkyl, e.g. $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexanyl, 1,8 diaza-spiro-[4,5]decyl, 1,7 diaza-spiro-[4,5]decyl, 1,6 diaza-spiro-[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro[5,4]decyl, 2,7 diaza-spiro[5,4]decyl, 3,8 diaza-spiro[5,4]decyl, 3,7 diaza-spiro[5,4]decyl, 1-aza-7,11-dioxo-spiro[5,5]undecyl, 1,4-diazabicyclo[2.2.2]oct-2-yl, tetrahydrofuran-2-yl, tetrahydrofuran-3-yl, tetrahydrothien-2-yl, tetrahydrothien-3-yl, piperazinyl, decahydroquinolinyl, decahydro-isoquinolinyl, decahydro-quinoxalinyl, or decahydro-quinazolinyl; an alicyclic system, which may comprise one or more heteroatoms preferably selected from the group consisting of O, S, or N; in particular 1,2-dihydropyridinyl, 1,2,5,6-tetrahydropyridinyl, 1,2,3,4-tetrahydropyridyl, 1,2-dihydropyrazyl, 1,2,3,4-tetrahydropyrazyl, cyclopropenyl, cyclobutenyl, cyclopentenyl, cyclohexenyl, cycloheptenyl; aryl, in particular phenyl, naphthalenyl or anthracenyl; or heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; optionally substituted; preferably hydrogen, alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; optionally substituted;

$R^5$ is selected from the group consisting of hydrogen; halogen, in particular F, Cl, Br or I; —$NO_2$; —CN; alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_1$-$C_6$ alkenyl, e.g. $C_1$, $C_2$, $C_3$, $C_4$, $C_5$, or $C_6$ alkenyl, preferably methenyl, ethenyl, 1-propenyl, 2-propenyl, 1-iso-propenyl, 2-iso-propenyl, 1-butenyl, 2-butenyl, 3-butenyl; cycloalkyl, e.g. $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantly, decahydro-naphthalenyl, 2-methylene-decahydro-naphthalenyl, or 2-methylene-decahydro-naphthalen-1-yl; alkoxy, in particular $C_1$-$C_6$ alkoxy, e.g. $C_1$, $C_2$, $C_3$, $C_4$, $C_5$, or $C_6$ alkoxy, preferably methoxy, ethoxy, propoxy, iso-propoxy, butoxy, iso-butoxy, tert-butoxy, pentoxy, or hexoxy; alkoxyalkyl, in particular $C_1$-$C_6$ alkoxy-$C_1$-$C_6$ alkyl, e.g. methoxymethyl, ethoxymethyl, propoxymethyl, methoxyethyl, ethoxyethyl, propoxyethyl, methoxypropyl, ethoxypropyl, or propoxypropyl; heterocycloalkyl, e.g. $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexanyl, 1,8 diaza-spiro-[4,5]decyl, 1,7 diaza-spiro-[4,5]decyl, 1,6 diaza-spiro-[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro-[5,4]decyl, 2,7 diaza-spiro[5,4]decyl, 3,8 diaza-spiro[5,4]decyl, 3,7 diaza-spiro[5,4]decyl, 1-aza-7,11-dioxo-spiro[5,5]undecyl, 1,4-diazabicyclo[2.2.2]oct-2-yl, tetrahydrofuran-2-yl, tetrahydrofuran-3-yl, tetrahydrothien-2-yl, tetrahydrothien-3-yl, piperazinyl, decahydroquinolinyl, decahydro-isoquinolinyl, decahydro-quinoxalinyl, or decahydro-quinazolinyl; an alicyclic system, which may comprise one or more heteroatoms preferably selected from the group consisting of O, S, or N; in particular 1,2-dihydropyridinyl, 1,2,5,6-tetrahydropyridinyl, 1,2,3,4-tetrahydropyridyl, 1,2-dihydropyrazyl, 1,2,3,4-tetrahydropyrazyl, cyclopropenyl, cyclobutenyl, cyclopentenyl, cyclohexenyl, cycloheptenyl; aryl, in particular phenyl, naphthalenyl or anthracenyl; or heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; optionally substituted; preferably hydrogen, alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; optionally substituted; optionally substituted;

$R^6$ is selected from the group consisting of is selected from the group consisting of hydrogen; halogen, in particular F, Cl, Br or I; —$NO_2$; —CN; alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_1$-$C_6$ alkenyl, e.g. $C_1$, $C_2$, $C_3$, $C_4$, $C_5$, or $C_6$ alkenyl, preferably methenyl, ethenyl, 1-propenyl, 2-propenyl, 1-iso-propenyl, 2-iso-propenyl, 1-butenyl, 2-butenyl, 3-butenyl; cycloalkyl, e.g. $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantly, decahydro-naphthalenyl, 2-methylene-decahydro-naphthalenyl, or 2-methylene-decahydro-naphthalen-1-yl; alkoxy, in particular $C_1$-$C_6$ alkoxy, e.g. $C_1$, $C_2$, $C_3$, $C_4$, $C_5$, or $C_6$ alkoxy, preferably methoxy, ethoxy, propoxy, iso-propoxy, butoxy, iso-butoxy, tert-butoxy, pentoxy, or hexoxy; alkoxyalkyl, in particular $C_1$-$C_6$ alkoxy-$C_1$-$C_6$ alkyl, e.g. methoxymethyl, ethoxymethyl, propoxymethyl, methoxyethyl, ethoxyethyl, propoxyethyl, methoxypropyl, ethoxypropyl, or propoxypropyl; heterocycloalkyl, e.g. $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexanyl, 1,8 diaza-spiro-[4,5]decyl, 1,7 diaza-spiro-[4,5]decyl, 1,6 diaza-spiro-[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro-[5,4]decyl, 2,7 diaza-spiro[5,4]decyl, 3,8 diaza-spiro[5,4]decyl, 3,7 diaza-spiro[5,4]decyl, 1-aza-7,11-dioxo-spiro[5,5]undecyl, 1,4-diazabicyclo[2.2.2]oct-2-yl, tetrahydrofuran-2-yl, tetrahydrofuran-3-yl, tetrahydrothien-2-yl, tetrahydrothien-3-yl, piperazinyl, decahydroquinolinyl, decahydro-isoquinolinyl, decahydro-quinoxalinyl, or decahydro-quinazolinyl; an alicyclic system, which may comprise one or more heteroatoms preferably selected from the group consisting of O, S, or N; in particular 1,2-dihydropyridinyl, 1,2,5,6-tetrahydropyridinyl, 1,2,3,4-tetrahydropyridyl, 1,2-dihydropyrazyl, 1,2,3,4-tetrahydropyrazyl, cyclopropenyl, cyclobutenyl, cyclopentenyl, cyclohexenyl, cycloheptenyl; aryl, in particular phenyl, naphthalenyl or anthracenyl; or heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; optionally substituted; preferably hydrogen, alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; optionally substituted;

or wherein $R^3$ and $R^4$ together form a heterocycloalkyl, preferably $C_5$-$C_{14}$-heterocycloalkyl, e.g. $C_5$, $C_6$, $C_7$, $C_8$, $C_9$, $C_{10}$, $C_{11}$, $C_{12}$, $C_{13}$ or $C_{14}$-heterocycloalkyl, in particular, imidazolidinyl, 1,3-diazacyclohexanyl, 1,3-diazacycloheptanyl, or decahydro-quinazolinyl; an alicyclic system comprising two nitrogen atoms indicated in formula (I) and which may comprise one or more further heteroatoms preferably selected from the group consisting of O, S, or N, preferably a 5, 6, 7, 8, 9, 10, 11, or 12 membered alicyclic ring system, in particular dihydro-imidazolyl, e.g. 1,2-dihydro-imidazolyl, dihydro-pyrimidinyl, e.g. 4,5, dihydro-pyrimidinyl, 1,2-dihydropyrimidinyl, 2,3-dihydro-1H-benzoimidazolyl, 2,3-dihydro-1H-imidazo[4,5-c]pyridinyl, 2,3-dihydro-1H-imidazo[4,5-d]pyridinyl, or 6,7-dihydro-5H-imidazo[4,5-c]pyridazinyl;

or wherein $R^5$ and $R^6$ together form a cycloalkyl, preferably $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantly, decahydro-naphthalenyl, 2-methylene-decahydro-naphthalenyl, or 2-methylene-decahydro-naphthalen-1-yl; heterocycloalkyl, e.g. $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexane, 1,8 diaza-spiro-[4,5]decyl, 1,7 diaza-spiro-[4,5]decyl, 1,6 diaza-spiro-[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro-[5,4]decyl, 2,7 diaza-spiro[5,4]decyl, 3,8 diaza-spiro[5,4]decyl, 3,7 diaza-spiro[5,4]decyl, 1-aza-7,11-dioxo-spiro[5,5]undecyl, 1,4-diazabicyclo[2.2.2]oct-2-yl, tetrahydrofuran-2-yl, tetrahydrofuran-3-yl, tetrahydrothien-2-yl, tetrahydrothien-3-yl, piperazinyl, decahydroquinolinyl, decahydro-isoquinolinyl, decahydro-quinoxalinyl, or decahydro-quinazolinyl; which may comprise one or more heteroatoms preferably selected from the group consisting of O, S, or N; in particular 1,2-dihydropyridinyl, 1,2,5,6-tetrahydropyridinyl, 1,2,3,4-tetrahydropyridyl, 1,2-dihydropyrazyl, 1,2,3,4-tetrahydropyrazyl, cyclopropenyl, cyclobutenyl, cyclopentenyl, cyclohexenyl, cycloheptenyl; aryl, in particular phenyl, naphthalenyl or anthracenyl; or heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; optionally substituted and
the bond indicated by the dashed line may be present or not, preferably this bond is present. In above indicated formulas (II) and (III) two additional tautomeric forms, i.e. isothiourea forms, are possible wherein the double bond is located between the carbon atom and either of the nitrogen atoms. These tautomeric forms are also comprised by the present invention. Whether a given compound will primarily be present in the thiourea or isothiourea form will depend on the groups flanking the respective nitrogen atom.

In a further preferred embodiment of the method of the invention, the potential antagonist has a structure according to formula (IV) or is a tautomer thereof:

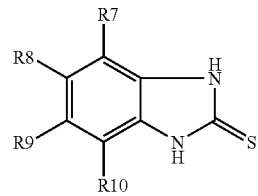

(IV)

wherein
$R^7$, $R^8$, $R^9$ and $R^{10}$ are in each instance independently selected from the group consisting of hydrogen, halogen, in particular F, Cl, Br or I; —$NO_2$; —CN; —$OR^{13}$; —$NR^{11}R^{12}$; —$COOR^{13}$; —$CONR^{11}R^{12}$; —$NR^{11}COR^{13}$; —$NR^{11}COR^{13}$; —$NR^{11}CONR^{11}R^{12}$; —$NR^{12}SO_2A$; —$COR^{13}$; —$SO_2NR^{11}R^{12}$; —$OOCR^{13}$; —$CR^{13}R^{14}OH$; $R^{13}OH$ and A, preferably hydrogen;

$R^{11}$ and $R^{12}$ is each independently selected from the group consisting of hydrogen, alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_2$-$C_6$ alkenyl, e.g. $C_2$, $C_3$, $C_4$, $C_5$, or $C_6$ alkenyl, preferably ethenyl, 1-propenyl, 2-propenyl, 1-iso-propenyl, 2-iso-propenyl, 1-butenyl, 2-butenyl, 3-butenyl; alkynyl, e.g. $C_2$, $C_3$, $C_4$, $C_5$, or $C_6$ alkynyl; cycloalkyl, in particular $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantly, or decahydro-naphthalenyl; heterocycloalkyl, e.g. $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexane, 1,8 diaza-spiro-[4,5]decyl, 1,7 diaza-spiro-[4,5]decyl, 1,6 diaza-spiro-[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro-[5,4]decyl, 2,7 diaza-spiro[5,4]decyl, 3,8 diaza-spiro[5,4]decyl, 3,7 diaza-spiro[5,4]decyl, 1-aza-7,11-dioxo-spiro[5,5]undecyl, 1,4-diazabicyclo[2.2.2]oct-2-yl, tetrahydrofuran-2-yl, tetrahydrofuranyl, tetrahydrothienyl, tetrahydrothienyl, piperazinyl, decahydroquinolinyl, decahydro-isoquinolinyl, decahydro-quinoxalinyl, decahydro-quinazolinyl; aryl, in particular phenyl, naphthalenyl or anthracenyl; heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; and aralkyl, preferably $C_1$-$C_6$ aralkyl, e.g. $C_1$, $C_2$, $C_3$, $C_4$, $C_5$, or $C_6$ aralkyl; or together form a heteroaryl, in particular, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, indolyl, isoindolyl, 1H-indazolyl, benzimidazolyl, indoxazinyl, 2,1-benzisoxazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; optionally substituted;

$R^{13}$ and $R^{14}$ is each independently selected from the group consisting of hydrogen; alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_2$-$C_6$ alkenyl, e.g. $C_2$, $C_3$, $C_4$, $C_5$, or $C_6$ alkenyl, preferably ethenyl, 1-propenyl, 2-propenyl, 1-iso-propenyl, 2-iso-propenyl, 1-butenyl, 2-butenyl, 3-butenyl; alkynyl, in particular $C_2$-$C_6$ alkynyl, e.g. $C_2$, $C_3$, $C_4$, $C_5$, or $C_6$ alkynyl; cycloalkyl, in particular $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantly, or decahydro-naphthalenyl; heterocycloalkyl, e.g. $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexane, 1,8 diaza-spiro-[4,5]decyl, 1,7 diaza-spiro-[4,5]decyl, 1,6 diaza-spiro-[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro-[5,4]decyl, 2,7 diaza-spiro[5,4]decyl, 3,8 diaza-spiro[5,4]decyl, 3,7 diaza-spiro[5,4]decyl, 1-aza-7,11-dioxo-spiro[5,5]undecyl, 1,4-diazabicyclo[2.2.2]oct-2-yl, tetrahydrofuran-2-yl, tetrahydrofuranyl, tetrahydrothienyl, tetrahydrothienyl, piperazinyl, decahydroquinolinyl, decahydro-isoquinolinyl, decahydro-quinoxalinyl, decahydro-quinazolinyl; alkoxy, in particular $C_1$-$C_6$ alkoxy, e.g. $C_1$, $C_2$, $C_3$, $C_4$, $C_5$, or $C_6$ alkoxy, preferably methoxy, ethoxy, propoxy, iso-propoxy, butoxy, iso-butoxy, tert-butoxy, pentoxy, or hexoxy; aryl, in particular phenyl, naphthalenyl or anthracenyl; aralkyl; preferably $C_1$-$C_6$ aralkyl, e.g. $C_1$, $C_2$, $C_3$, $C_4$, $C_5$, or $C_6$ aralkyl; heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; and —$NR^{11}R^{12}$;

A is selected from the group consisting of alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_1$-$C_6$ alkenyl, e.g. $C_1$, $C_2$, $C_3$, $C_4$, $C_5$, or $C_6$ alkenyl, preferably methenyl, ethenyl, 1-propenyl, 2-propenyl, 1-iso-propenyl, 2-iso-propenyl, 1-butenyl, 2-butenyl, 3-butenyl; alkynyl, e.g. $C_2$, $C_3$, $C_4$, $C_5$, or $C_6$ alkynyl; cycloalkyl, in particular $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantly, decahydro-naphthalenyl; alkoxy, in particular $C_1$-$C_6$ alkoxy, e.g. $C_1$, $C_2$, $C_3$, $C_4$, $C_5$, or $C_6$ alkoxy, preferably methoxy, ethoxy, propoxy, iso-propoxy, butoxy, iso-butoxy, tert-butoxy, pentoxy, or hexoxy; alkoxyalkyl, in particular $C_1$-$C_6$-alkoxy-$C_1$-$C_6$-alkyl, e.g. methoxymethyl, ethoxymethyl, propoxymethyl, methoxyethyl, ethoxyethyl, propoxyethyl, methoxypropyl, ethoxypropyl, or propoxypropyl; heterocycloalkyl, e.g. $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexane, 1,8 diaza-spiro-[4,5]decyl, 1,7 diaza-spiro-[4,5]decyl, 1,6 diaza-spiro-[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro-[5,4]decyl, 2,7 diaza-spiro[5,4]decyl, 3,8 diaza-spiro[5,4]decyl, 3,7 diaza-spiro[5,4]decyl, 1-aza-7,11-dioxo-spiro[5,5]undecyl, 1,4-diazabicyclo[2.2.2]oct-2-yl, tetrahydrofuran-2-yl, tetrahydrofuranyl, tetrahydrothienyl, tetrahydrothienyl, piperazinyl, decahydroquinolinyl, decahydro-isoquinolinyl, decahydro-quinoxalinyl, decahydro-quinazolinyl; an alicyclic system, which may comprise one or more heteroatoms, e.g. 1, 2, 3, or 4, preferably selected from the group consisting of O, S, or N; in particular 1,2-dihydropyridinyl, 1,2,5,6-tetrahydropyridinyl, 1,2,3,4-tetrahydropyridyl, 1,2-dihydropyrazyl, 1,2,3,4-tetrahydropyrazyl, cyclopropenyl, cyclobutenyl, cyclopentenyl, cyclohexenyl, cycloheptenyl; aryl, in particular phenyl, naphthalenyl or anthracenyl; and heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; optionally substituted. In above indicated formulas (IV) two additional tautomeric forms, i.e. isothiourea forms, are possible wherein the double bond is located between the carbon atom and either of the nitrogen atoms. These tautomeric forms are also comprised by the present invention.

The potential antagonists, which are employed in the methods of the present invention can be synthesized by methods and standard procedures known to those skilled in the art, i.e. as described in the literature (for example in the standard works, such as Houben-Weyl, Methoden der organischen Chemie [Methods of Organic Chemistry], Georg-Thieme-Verlag, Stuttgart), to be precise under reaction conditions which are known to those skilled in the art and suitable for the said reactions.

The selected, e.g. isolated, antagonist is in a preferred embodiment chemical modified in a further step. Again this chemical modification can be effected by a variety of methods known in the art, which include without limitation the introduction of one or more, preferably two, three or four substituents or the exchange of one or more substituents. Preferably, the introduction or exchange of one or two in each instance independently selected from the group consisting of halogen, in particular F, Cl, Br or I; —$NO_2$; —CN; —$OR^c$; —$NR^aR^b$; —$COOR^c$; —$CONR^aR^b$; —$NR^aCOR^c$; —$NR^aCOR^c$; —$NR^aCONR^aR^b$; —$NR^aSO_2B$; —$COR^c$; —$SO_2NR^aR^b$; —$OOCR^c$; —$CR^cR^dOH$; —$R^cOH$; and —B;

- $R^a$ and $R^b$ is each independently selected from the group consisting of hydrogen; alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_2$-$C_6$ alkenyl, e.g. $C_2$, $C_3$, $C_4$, $C_5$, or $C_6$ alkenyl, preferably ethenyl, 1-propenyl, 2-propenyl, 1-iso-propenyl, 2-iso-propenyl, 1-butenyl, 2-butenyl, 3-butenyl; alkynyl, in particular $C_2$-$C_6$ alkynyl, e.g. $C_2$, $C_3$, $C_4$, $C_5$, or $C_6$ alkynyl; cycloalkyl, in particular $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantly, decahydro-naphthalenyl; heterocycloalkyl, e.g. $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexane, 1,8 diaza-spiro-[4,5]decyl, 1,7 diaza-spiro-[4,5]decyl, 1,6 diaza-spiro-[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro-[5,4]decyl, 2,7 diaza-spiro[5,4]decyl, 3,8 diaza-spiro[5,4]decyl, 3,7 diaza-spiro[5,4]decyl, 1-aza-7,11-dioxo-spiro[5,5]undecyl, 1,4-diazabicyclo[2.2.2]oct-2-yl, tetrahydrofuran-2-yl, tetrahydrofuranyl, tetrahydrothienyl, tetrahydrothienyl, piperazinyl, decahydroquinolinyl, decahydro-isoquinolinyl, decahydro-quinoxalinyl, decahydro-quinazolinyl; alkoxy, in particular $C_1$-$C_6$ alkoxy, e.g. $C_1$, $C_2$, $C_3$, $C_4$, $C_5$, or $C_6$ alkoxy, preferably methoxy, ethoxy, propoxy, iso-propoxy, butoxy, iso-butoxy, tert-butoxy, pentoxy, or hexoxy; aryl, in particular phenyl, naphthalenyl or anthracenyl; aralkyl; preferably $C_1$-$C_6$ aralkyl, e.g. $C_1$, $C_2$, $C_3$, $C_4$, $C_5$, or $C_6$ aralkyl; heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; and —$NR^cR^d$;
- $R^c$ and $R^d$ is each independently selected from the group consisting of hydrogen, alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_2$-$C_6$ alkenyl, e.g. $C_2$, $C_3$, $C_4$, $C_5$, or $C_6$ alkenyl, preferably ethenyl, 1-propenyl, 2-propenyl, 1-iso-propenyl, 2-iso-propenyl, 1-butenyl, 2-butenyl, 3-butenyl; alkynyl, e.g. $C_2$, $C_3$, $C_4$, $C_5$, or $C_6$ alkynyl; cycloalkyl, in particular $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantly, decahydro-naphthalenyl; heterocycloalkyl, e.g. $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexane, 1,8 diaza-spiro-[4,5]decyl, 1,7 diaza-spiro-[4,5]decyl, 1,6 diaza-spiro-[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro-[5,4]decyl, 2,7 diaza-spiro[5,4]decyl, 3,8 diaza-spiro[5,4]decyl, 3,7 diaza-spiro[5,4]decyl, 1-aza-7,11-dioxo-spiro[5,5]undecyl, 1,4-diazabicyclo[2.2.2]oct-2-yl, tetrahydrofuran-2-yl, tetrahydrofuranyl, tetrahydrothienyl, tetrahydrothienyl, piperazinyl, decahydroquinolinyl, decahydro-isoquinolinyl, decahydro-quinoxalinyl, decahydro-quinazolinyl; aryl, in particular phenyl, naphthalenyl or anthracenyl; heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; and aralkyl, preferably $C_1$-$C_6$ aralkyl, e.g. $C_1$, $C_2$, $C_3$, $C_4$, $C_5$, or $C_6$ aralkyl; or together form a heteroaryl, in particular, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, indolyl, isoindolyl, 1H-indazolyl, benzimidazolyl, indoxazinyl, 2,1-benzisoxazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; optionally substituted; and B is selected from the group consisting of alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_1$-$C_6$ alkenyl, e.g. $C_1$, $C_2$, $C_3$, $C_4$, $C_5$, or $C_6$ alkenyl, preferably methenyl, ethenyl, 1-propenyl, 2-propenyl, 1-iso-propenyl, 2-iso-propenyl, 1-butenyl, 2-butenyl, 3-butenyl; alkynyl, e.g. $C_2$, $C_3$, $C_4$, $C_5$, or $C_6$ alkynyl; cycloalkyl, in particular $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantly, decahydro-naphthalenyl; alkoxy, in particular $C_1$-$C_6$ alkoxy, e.g. $C_1$, $C_2$, $C_3$, $C_4$, $C_5$, or $C_6$ alkoxy, preferably methoxy, ethoxy, propoxy, iso-propoxy, butoxy, iso-butoxy, tert-butoxy, pentoxy, or hexoxy; alkoxyalkyl, in particular $C_1$-$C_6$-alkoxy-$C_1$-$C_6$-alkyl, e.g. methoxymethyl, ethoxymethyl, propoxymethyl, methoxyethyl, ethoxyethyl, propoxyethyl, methoxypropyl, ethoxypropyl, or propoxypropyl; heterocycloalkyl, e.g. $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexane, 1,8 diaza-spiro-[4,5]decyl, 1,7 diaza-spiro-[4,5]decyl, 1,6 diaza-spiro-[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro-[5,4]decyl, 2,7 diaza-spiro[5,4]decyl, 3,8 diaza-spiro[5,4]decyl, 3,7 diaza-spiro[5,4]decyl, 1-aza-7,11-dioxo-spiro[5,5]undecyl, 1,4-diazabicyclo[2.2.2]oct-2-yl, tetrahydrofuran-2-yl, tetrahydrofuranyl, tetrahydrothienyl, tetrahydrothienyl, piperazinyl, decahydroquinolinyl, decahydro-isoquinolinyl, decahydro-quinoxalinyl, decahydro-quinazolinyl; an alicyclic system, which may comprise one or more heteroatoms, e.g. 1, 2, 3, or 4, preferably selected from the group consisting of O, S, or N; in particular 1,2-dihydropyridinyl, 1,2,5,6-tetrahydropyridinyl, 1,2,3,4-tetrahydropyridyl, 1,2-dihydropyrazyl, 1,2,3,4-tetrahydropyrazyl, cyclopropenyl, cyclobutenyl, cyclopentenyl, cyclohexenyl, cycloheptenyl; aryl, in particular phenyl, naphthalenyl or anthracenyl; and heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; optionally substituted.

The thus modified antagonist is then tested with the first embodiment of the method of the present invention. The modified antagonist is contacted with the hTAS2R38 polypeptide as such or with the polypeptide expressed in a host cell, which has been contacted prior, concomitantly or after step (1) with an agonist of bitter taste receptor hTAS2R38 or a structurally related agonist thereof and subsequently inhibition of the bitter taste receptor activity by the modified antagonist is measured. The inhibition of activation of the hTAS2R38, protein can be measured, e.g. by the intracellular calcium release mediated. If needed the steps of selecting the antagonist, modifying the compound, contacting the antagonist with a polypeptide or a host cell and measuring of the inhibition of the bitter taste receptor activity can be repeated a further or any given number of times as required. The above described method is also termed "directed evolution" of an antagonist since it involves a multitude of steps including modification and selection, whereby antagonizing compounds are selected in an "evolutionary" process optimizing their capabilities with respect to a particular property, e.g. their ability to inhibit the activity of hTAS2R38, in particular inhibit the intracellular release of calcium. Preferably, a modified antagonist is selected that reduces the activity of hTAS2R38, stimulated by a hTAS2R38 agonist at least as good as the identified antagonist used as basis for the modified antagonist at the same molar concentration. More preferably, the modified antagonist shows a stronger reduction at the same molar concentration, preferably at least a 10% stronger reduction, 20%, 30%, 40%, 50%, 60, or 70% stronger reduction.

In a preferred embodiment an antagonist selected from the group of N,N'-diethylthiourea, N,N'-dimethylthiourea, 2-mercaptobenzimidazole or compounds structurally related thereto are used in the first round of above stated directed evolution methods.

The term "structurally related antagonist" is a substance, which is derived from N,N'-diethylthiourea, N,N'-dimethylthiourea and 2-mercaptobenzimidazole, respectively, by 1, 2, 3, 4, 5 or 6 steps of chemical modification and which lowers the hTAS2R38 bitter taste receptor activity compared to the activity determined in the presence of N,N'-diethylthiourea, N,N'-dimethylthiourea and 2-mercaptobenzimidazole, respectively, by at least 10% (e.g. at least 10%, 15%, 20%, 30%, 40%, 50%, 60%, 70%, 80%, 90%, 95%, 98%, 99%, 99.5% or 100%) Preferably, the antagonistic derivative exerts this action, when it is contacted prior, concomitantly or after, preferably concomitantly, to the contacting of the hTAS2R38 polypeptide, the host cell expressing the hTAS2R38 polypeptide, or the vector comprising the hTAS2R38 polypeptide, with a hTAS2R38 agonist. Preferred structurally related antagonists have a structure as described above under formulas (I) to (IV).

In order to express cDNAs encoding the receptors, one typically subclones receptor cDNA into an expression vector that contains a strong promoter to direct transcription, a transcription/translation terminator, and a ribosome-binding site for translational initiation. Suitable bacterial promoters are well known in the art, e.g., *E. coli, Bacillus* sp., and *Salmonella*, and kits for such expression systems are commercially available. Similarly eukaryotic expression systems for mammalian cells, yeast, and insect cells are well known in the art and are also commercially available. The eukaryotic expression vector may be, for example an adenoviral vector, an adeno-associated vector, or a retroviral vector.

In addition to the promoter, the expression vector typically contains a transcription unit or expression cassette that contains all the additional elements required for the expression of the receptor-encoding nucleic acid in host cells. A typical expression cassette thus contains a promoter operatively linked to the nucleic acid sequence encoding the receptor and signals required for efficient polyadenylation of the transcript, ribosome binding sites, and translation termination. The nucleic acid sequence encoding the receptor may typically be linked to a membrane-targeting signal such as the N-terminal 45 amino acids of the rat somatostatin receptor 3 sequence to promote efficient cell-surface expression of the recombinant receptor. Additional elements of the cassette may include, for example enhancers.

An expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ, but there are many more known in the art to the skilled person that can be usefully employed.

Expression vectors containing regulatory elements from eukaryotic viruses are typically used in eukaryotic expression vectors, e.g. SV40 vectors, papilloma virus vectors, and vectors derived from Epstein-Barr virus. Other exemplary eukaryotic vectors include pMSG, pAV009/A.sup.+, pMTO10/A.sup.+, pMAMneo-5, baculovirus pDSVE, pcDNA3.1, pIRES and any other vector allowing expression of proteins under the direction of the SV40 early promoter, SV40 late promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase, hygromycin B phosphotransferase, and dihydrofolate reductase. Alternatively, high yield expression systems not involving gene amplification are also suitable.

The elements that are typically included in expression vectors also include a replicon that functions in *E. coli*, a gene encoding drug resistance to permit selection of bacteria that harbor recombinant plasmids, and unique restriction sites in nonessential regions of the plasmid to allow insertion of eukaryotic sequences. The particular drug resistance gene chosen is not critical, any of the many drug resistance genes known in the art are suitable. The prokaryotic sequences are optionally chosen such that they do not interfere with the replication of the DNA in eukaryotic cells, if necessary.

Standard transfection methods can be used to produce bacterial, mammalian, yeast or insect cell lines that express large quantities of the receptor, which are then purified using standard techniques. Any of the well-known procedures for introducing foreign polynucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell. It is only necessary that the particular genetic engineering procedure used be capable of successfully introducing at least one gene into the host cell capable of expressing the receptor.

After the expression vector is introduced into the cells, the transfected cells may be cultured under conditions favouring expression of the receptor, which is recovered from the culture using standard techniques. For example the cells may be burst open either mechanically or by osmotic shock before being subject to precipitation and chromatography steps, the nature and sequence of which will depend on the particular recombinant material to be recovered. Alternatively, the recombinant protein may be recovered from the culture medium in which the recombinant cells had been cultured.

The activity of the receptor described herein can be assessed using a variety of in vitro and in vivo assays to determine functional, chemical, and physical effects, e.g., measuring ligand binding, secondary messengers (e.g., cAMP, cGMP, IP$_3$, DAG, or Ca$^{2+}$) ion flux, phosphorylation levels, transcription levels, of reporter constructs neurotransmitter levels, and the like. Such assays are used in the method of the present invention to test for the activity of the receptors.

The effects of the test compounds upon the function of the receptors can be measured by examining any of the parameters described above. Any suitable physiological change that affects receptor activity can be used to assess the influence of a test compound on the receptors usable in the methods of this invention. When the functional consequences are determined using intact cells or animals, these consequences can be measured by any means known to those skilled in the art, e.g., patch clamping, voltage-sensitive dyes, whole cell currents, radioisotope efflux, inducible markers, oocyte bitter taste receptor gene expression; tissue culture cell bitter taste receptor expression; transcriptional activation of bitter taste receptor genes; ligand binding assays; voltage, membrane potential and conductance changes; ion, preferably sodium or calcium ion flux assays, for example measuring calcium levels using calcium sensitive dyes such as Fluo-3, Fluo-4 or Fura-2; changes in intracellular second messengers such as cAMP, cGMP, and inositol triphosphate (IP$_3$); changes in intracellular calcium levels; neurotransmitter release, and the like. These assays may be performed on intact cells expressing a bitter taste receptor polypeptide, on permeabilized cells, or on membrane fractions produced by standard methods.

Preferred assays for G-protein coupled receptors include cells that are loaded with ion sensitive dyes to report receptor activity. In assays for identifying modulatory compounds, changes in the level of ions in the cytoplasm or membrane voltage will be monitored using an ion sensitive or membrane voltage fluorescent indicator, respectively. For G-protein coupled receptors, promiscuous G-proteins such as G$\alpha$i5 and G$\alpha$i6 and chimeric G-proteins can be used in the assay of choice (see, for example, Wilkie et al. (1991) Proc. Nat. Acad. Sci. USA 88: 10049-10053). Such promiscuous G-proteins allow coupling of a wide range of receptors to G-protein dependent signal pathways.

Receptor activation typically initiates subsequent intracellular events, e.g. increases in second messengers such as IP$_3$, which releases intracellular stores of calcium ions. Activation of some G-protein coupled receptors stimulates the formation of inositol trisphosphate through phospholipase C-mediated hydrolysis of phosphatidylinositol bisphosphate (Berridge & Irvine (1984) Nature 312: 315-21). IP$_3$ in turn stimulates the release of intracellular calcium ion stores. Thus, a change in cytoplasmic calcium ion levels, or a change in second messenger levels such as IP$_3$ can be used to assess G-protein coupled receptor function. Cells expressing such G-protein coupled receptors may exhibit increased cytoplasmic calcium levels as a result of contribution from both intracellular stores and via activation of ion channels, in which case it may be desirable, although not necessary, to conduct such assays in calcium-free buffer, optionally supplemented with a chelating agent such as EGTA, to distinguish fluorescence response resulting from calcium release from internal stores.

In a preferred embodiment, receptor activity is measured by expressing the hTAS2R38 bitter taste receptors in a heterologous cell with a G-protein, such as G$\alpha$15, G$\alpha$16, transducin, gustducin, or a chimeric G-protein that links the receptor to a phospholipase C signal transduction pathway. In another aspect of the invention, only the extracellular domain of the respective bitter taste receptor is expressed as a chimeric transmembrane fusion protein. A preferred cell line is HEK-293, although other mammalian cell lines are also preferred such as CHO and COS cells. Modulation of taste transduction is assayed by measuring changes in intracellular $Ca^{2+}$ levels, which change in response to modulation of the receptor signal transduction pathway via administration of a molecule that associates with the receptor. Changes in $Ca^{2+}$ levels are optionally measured using fluorescent $Ca^{2+}$ indicator dyes and fluorometric imaging. The activity of the signaling molecule and the increase or decrease of that activity in response to the potential antagonist can be determined as outlined above with respect to the identification of bitter taste receptor taste activity. The respectively indicated percent decreases of the activity, which are required to qualify as antagonist do apply mutatis mutandis. Additionally the term "contacting" has the meaning as outlined above. Preferably the signaling molecule and/or the promiscuous G-protein has been introduced into the cell. The types of cell lines, which are preferred are those indicated above.

In yet another embodiment, the ligand-binding domains of the receptors can be employed in vitro in soluble or solid-state reactions to assay for ligand binding. Ligand binding to a bitter taste receptor, or a domain of a bitter taste receptor, such as e.g. the extracellular domain, can be tested in solution, in a bilayer membrane attached to a solid phase, in a lipid monolayer or vesicles. Thereby, the binding of a modulator to the receptor, or domain, can be observed using changes in spectroscopic characteristics, e.g. fluorescence, fluorescence polarization, plasmon resonance, absorbance or refractive index; or hydrodynamic (e.g. shape), chromatographic, or solubility properties, as is generally known in the art.

The compounds tested as modulators, i.e. potential agonists and antagonists, of the receptors can be any small chemical compound, or a biological entity, such as a protein, sugar, nucleic acid or lipid. Typically, test compounds will be small chemical molecules. Essentially any chemical compound can be used as a potential modulator or ligand in the assays of the invention, although knowledge of the ligand specificity of an individual receptor would enable the skilled person to make an intelligent selection of interesting compounds. The assays may be designed to screen large chemical libraries by automating the assay steps and providing compounds from any convenient source to assays, which are typically run in parallel (e.g., in microtiter formats on microtiter plates in robotic assays). The skilled person will understand that there are many suppliers of libraries of chemical compounds.

Assays may be run in high throughput screening methods that involve providing a combinatorial chemical or peptide library containing a large number of potential therapeutic, or tastant compounds (that are potential ligand compounds). Such libraries are then screened in one or more assays, as described herein, to identify those library members (particular chemical species or subclasses) that display a desired characteristic activity. The compounds thus identified can serve as lead compounds to further develop modulators for final products, or can themselves be used as actual modulators. A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art and no more needs to be stated here.

In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100 to about 1500 different compounds. It is possible to assay several different plates per day; assay screens for up to about 6,000-20,000 different compounds are possible using the integrated systems of the invention.

Antagonists identified by method described herein above can be administered directly to a human subject to modulate, e.g. inhibit, bitter taste. Alternatively, such compounds can be formulated with other ingredients of preparations to be taken orally, for example, foods, including animal food, and beverages, pharmaceutical or nutraceutical or homeopathic preparations.

Therefore, another aspect of the invention is a method for the production of food, a food precursor material or additive employed in the production of foodstuff comprising the step of admixing an antagonist isolated by the method of the invention or a modified antagonist obtainable by the methods of the invention, N,N'-diethylthiourea, N,N'-dimethylthiourea, 2-mercaptobenzimidazole or an antagonist structurally related thereto with foodstuff, a food precursor material or additive employed in the production of foodstuff. Preferred antagonists used in this method have a structure according to formula (I) or are tautomers thereof,

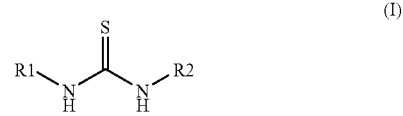

(I)

wherein;

R¹ is selected from the group consisting of alkyl, alkenyl, alkynyl, cycloalkyl, alkoxy, alkoxyalkyl, heterocycloalkyl, an alicyclic system, aryl and heteroaryl; optionally substituted;

R² is selected from the group consisting of alkyl, alkenyl, alkynyl, cycloalkyl, alkoxy, alkoxyalkyl, heterocycloalkyl, an alicyclic system, aryl and heteroaryl; optionally substituted;

or

R¹ and R² together form a heterocycloalkyl, an alicyclic system or heteroaryl.

More preferred antagonists used in this method have a structure according to formula (II) or formula (III) or are a tautomers thereof:

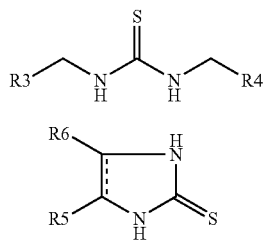

wherein $R^3$ is selected from the group consisting of alkyl, alkenyl, alkynyl, cycloalkyl, alkoxy, alkoxyalkyl, heterocycloalkyl, an alicyclic system, aryl and heteroaryl; optionally substituted;

$R^4$ is selected from the group consisting of hydrogen, alkyl, alkenyl, alkynyl, cycloalkyl, alkoxy, alkoxyalkyl, heterocycloalkyl, an alicyclic system, aryl and heteroaryl; optionally substituted $R^5$ is selected from the group consisting of hydrogen, halogen, —$NO_2$; —CN; alkyl, alkenyl, cycloalkyl, alkoxy, alkoxyalkyl, heterocycloalkyl, an alicyclic system, aryl and heteroaryl; optionally substituted;

$R^6$ is selected from the group consisting of alkyl, alkenyl, cycloalkyl, alkoxy, alkoxyalkyl, heterocycloalkyl, an alicyclic system, aryl and heteroaryl; optionally substituted;

or wherein $R^3$ and $R^4$ together form a heterocycloalkyl, or an alicyclic system;

or wherein $R^5$ and $R^6$ together form a cycloalkyl, heterocycloalkyl, an alicyclic system, aryl or heteroaryl; and the bond indicated by the dashed line may be present or not.

Further preferred antagonists usable in this method have a structure according to formula (IV) or are tautomers thereof:

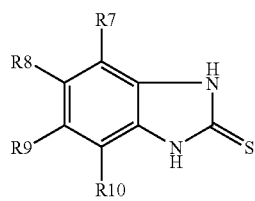

wherein $R^7$, $R^8$, $R^9$ and $R^{10}$ are in each instance independently selected from the group consisting of hydrogen, halogen, in particular F, Cl, Br or I; —$NO_2$; —CN; —$OR^{13}$; —$NR^{11}R^{12}$; —$COOR^{13}$; —$CONR^{11}R^{12}$; —$NR^{11}COR^{13}$; —$NR^{11}COR^{13}$; —$NR^{11}CONR^{11}R^{12}$; —$NR^{11}SO_2A$; —$COR^{13}$; —$SO_2NR^{11}R^{12}$; —$OOCR^{13}$; —$CR^{13}R^{14}OH$; $R^{13}OH$ and A, preferably hydrogen;

$R^{11}$ and $R^{12}$ is each independently selected from the group consisting of hydrogen, alkyl, alkenyl, alkynyl, cycloalkyl, heterocycloalkyl, aryl, heteroaryl, and aralkyl or together form a heteroaryl, or heterocycloalkyl;

$R^{13}$ and $R^{14}$ is each independently selected from the group consisting of hydrogen, alkyl, alkenyl, alkynyl, cycloalkyl, heterocycloalkyl, alkoxy, aryl, aralkyl, heteroaryl, and —$NR^{11}R^{12}$; and A is selected from the group consisting of alkyl, alkenyl, cycloalkyl, alkoxy, alkoxyalkyl, heterocycloalkyl, an alicyclic system, aryl and heteroaryl; optionally substituted.

In above formulas (I), (II), (III), and (IV) the substituents $R^1, R^2, R^3, R^4, R^5, R^6, R^7, R^8, R^9, R^{10}, R^{11}, R^{12}, R^{13}, R^{14}$, and A have the preferred and particularly preferred meanings indicated above with respect to the method of isolating an antagonist. The term antagonist has the meaning as defined above.

Consequently, a further aspect of the invention is a foodstuff, any foodstuff precursor material or additive employed in the production of foodstuff producible as stated above.

Bitter taste is a particular problem when orally administering pharmaceuticals, which often have an unpleasant bitter taste. In particular in elderly persons, children and chronically ill patients this taste can lead to a lack of compliance with a treatment regimen. In addition in veterinary applications the oral administration of bitter tasting pharmaceuticals can be problematic. Therefore, a further aspect of the invention is a method for the production of a nutraceutical or pharmaceutical composition comprising the step of admixing the antagonist isolated and/or modified by the method of the invention, N,N'-diethylthiourea, N,N'-dimethylthiourea, 2-mercaptobenzimidazole or an antagonist structurally related thereto with an active agent and optionally with a pharmaceutically acceptable carrier and/or adjuvants. Preferably, further comprising the step of formulating the pharmaceutical composition into a pharmaceutically acceptable form. Preferred antagonists used in this method have a structure according to formula (I) or are tautomers thereof,

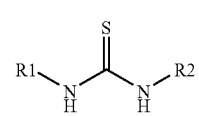

wherein;

$R^1$ is selected from the group consisting of alkyl, alkenyl, alkynyl, cycloalkyl, alkoxy, alkoxyalkyl, heterocycloalkyl, an alicyclic system, aryl and heteroaryl; optionally substituted;

$R^2$ is selected from the group consisting of alkyl, alkenyl, alkynyl, cycloalkyl, alkoxy, alkoxyalkyl, heterocycloalkyl, an alicyclic system, aryl and heteroaryl; optionally substituted;

or $R^1$ and $R^2$ together form a heterocycloalkyl, an alicyclic system or heteroaryl.

More preferred antagonists used in this method have a structure according to formula (II) or formula (III) or are a tautomers thereof:

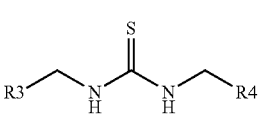

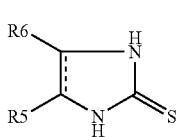

(III)

wherein

R³ is selected from the group consisting of alkyl, alkenyl, alkynyl, cycloalkyl, alkoxy, alkoxyalkyl, heterocycloalkyl, an alicyclic system, aryl and heteroaryl; optionally substituted;

R⁴ is selected from the group consisting of hydrogen, alkyl, alkenyl, alkynyl, cycloalkyl, alkoxy, alkoxyalkyl, heterocycloalkyl, an alicyclic system, aryl and heteroaryl; optionally substituted R⁵ is selected from the group consisting of hydrogen, halogen, —NO₂; —CN; alkyl, alkenyl, cycloalkyl, alkoxy, alkoxyalkyl, heterocycloalkyl, an alicyclic system, aryl and heteroaryl; optionally substituted;

R⁶ is selected from the group consisting of alkyl, alkenyl, cycloalkyl, alkoxy, alkoxyalkyl, heterocycloalkyl, an alicyclic system, aryl and heteroaryl; optionally substituted;

or wherein R³ and R⁴ together form a heterocycloalkyl, or an alicyclic system;

or wherein R⁵ and R⁶ together form a cycloalkyl, heterocycloalkyl, an alicyclic system, aryl or heteroaryl; and the bond indicated by the dashed line may be present or not.

Further preferred antagonists usable in this method have a structure according to formula (IV) or are tautomers thereof:

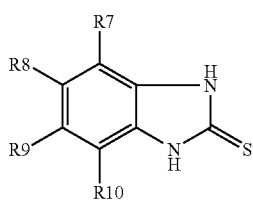

(IV)

wherein

R⁷, R⁸, R⁹ and R¹⁰ are in each instance independently selected from the group consisting of hydrogen, halogen, in particular F, Cl, Br or I; —NO₂; —CN; —OR¹³; —NR¹¹R¹²; —COOR¹³; —CONR¹¹R¹²; —NR¹¹COR¹³; —NR¹¹COR¹³; —NR¹¹CONR¹¹R¹²; —NR¹¹SO₂A; —COR¹³; —SO₂NR¹¹R¹²; —OOCR¹³; —CR¹³R¹⁴OH; R¹³OH and A, preferably hydrogen;

R¹¹ and R¹² is each independently selected from the group consisting of hydrogen, alkyl, alkenyl, alkynyl, cycloalkyl, heterocycloalkyl, aryl, heteroaryl, and aralkyl or together form a heteroaryl, or heterocycloalkyl;

R¹³ and R¹⁴ is each independently selected from the group consisting of hydrogen, alkyl, alkenyl, alkynyl, cycloalkyl, heterocycloalkyl, alkoxy, aryl, aralkyl, heteroaryl, and —NR¹¹R¹²; and A is selected from the group consisting of alkyl, alkenyl, cycloalkyl, alkoxy, alkoxyalkyl, heterocycloalkyl, an alicyclic system, aryl and heteroaryl; optionally substituted.

In above formulas (I), (II), (III), and (IV) the substituents R¹, R², R³, R⁴, R⁵, R⁶, R⁷, R⁸, R⁹, R¹⁰, R¹¹, R¹², R¹³, R¹⁴, and A have the preferred and particularly preferred meanings indicated above with respect to the method of isolating an antagonist. The term antagonist has the meaning as defined above.

Also comprised is a nutraceutical or pharmaceutical composition producible according to the method of the invention, comprising at least one nutraceutically or pharmaceutically active agent, and optionally one or more pharmaceutically acceptable carrier and/or adjuvant. These pharmaceutical and nutraceutical compositions comprise both products for human and animal consumption.

The amount of the antagonistic compound of present invention to be taken orally must be sufficient to effect a beneficial response in the subject, preferably human subject, and will be determined by the efficacy of the particular taste modulators and the existence, nature, and extent of any adverse side-effects that accompany the administration of a particular compound. As mentioned before, the hTAS2R38 antagonists N,N'-dimethylthiourea and 2-mercaptobenzimidazole can act as agonists for human bitter taste receptor hTAS2R38 at low concentrations. Therefore, the antagonist N,N'-dimethylthiourea or a structurally related antagonist, is preferably comprised in the nutraceutical or pharmaceutical composition, in food, a food precursor material or food additive in a concentration higher than 3 mM, preferably higher than 10 mM, preferably higher than 30 mM. The concentration of 2-mercaptobenzimidazole or a structurally related antagonist is higher than 0.01 mM, preferably higher than 0.1 mM, more preferably higher than 1 mM.

A further aspect of the present invention is the use of an antagonist of hTAS2R38 bitter taste receptor activity isolated according to the method of the invention or a modified antagonist of hTAS2R38 producible according to the method of the invention to reduce or suppress bitter taste. In this use the bitter taste is preferably mediated by the bitter taste receptor hTAS2R38. This use further preferably comprises the use of to suppress bitter taste of a nutraceutical composition, of a pharmaceutical composition, of food, of a food precursor material or of a food additive. In a preferred use the antagonist has a structure according to formula (I) or is a tautomer thereof,

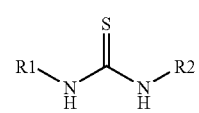

(I)

wherein;

R¹ is selected from the group consisting of alkyl, alkenyl, alkynyl, cycloalkyl, alkoxy, alkoxyalkyl, heterocycloalkyl, an alicyclic system, aryl and heteroaryl; optionally substituted;

R² is selected from the group consisting of alkyl, alkenyl, alkynyl, cycloalkyl, alkoxy, alkoxyalkyl, heterocycloalkyl, an alicyclic system, aryl and heteroaryl; optionally substituted;

or

R¹ and R² together form a heterocycloalkyl, an alicyclic system or heteroaryl.

In a more preferred use the antagonist has a structure according to formula (II) or formula (III) or is a tautomer thereof:

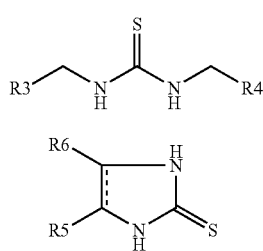

wherein
R³ is selected from the group consisting of alkyl, alkenyl, alkynyl, cycloalkyl, alkoxy, alkoxyalkyl, heterocycloalkyl, an alicyclic system, aryl and heteroaryl; optionally substituted;
R⁴ is selected from the group consisting of hydrogen, alkyl, alkenyl, alkynyl, cycloalkyl, alkoxy, alkoxyalkyl, heterocycloalkyl, an alicyclic system, aryl and heteroaryl; optionally substituted
R⁵ is selected from the group consisting of hydrogen, halogen, —NO₂; —CN; alkyl, alkenyl, cycloalkyl, alkoxy, alkoxyalkyl, heterocycloalkyl, an alicyclic system, aryl and heteroaryl; optionally substituted;
R⁶ is selected from the group consisting of alkyl, alkenyl, cycloalkyl, alkoxy, alkoxyalkyl, heterocycloalkyl, an alicyclic system, aryl and heteroaryl; optionally substituted;
or wherein R³ and R⁴ together form a heterocycloalkyl, or an alicyclic system;
or wherein R⁵ and R⁶ together form a cycloalkyl, heterocycloalkyl, an alicyclic system, aryl or heteroaryl; and
the bond indicated by the dashed line may be present or not.
In a further preferred use the antagonist has a structure according to formula (IV) or is a tautomer thereof:

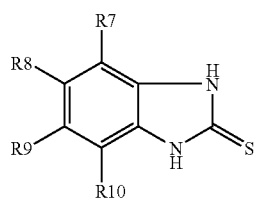

wherein
R⁷, R⁸, R⁹ and R¹⁰ are in each instance independently selected from the group consisting of hydrogen, halogen, in particular F, Cl, Br or I; —NO₂; —CN; —OR¹³; —NR¹¹R¹²; —COOR¹³; —CONR¹¹R¹²; —NR¹¹COR¹³; —NR¹¹COR¹³; —NR¹¹CONR¹¹R¹²; —NR¹¹SO₂A; —COR¹³; —SO₂NR¹¹R¹²; —OOCR¹³; —CR¹³R¹⁴OH; R¹³OH and A, preferably hydrogen;
R¹¹ and R¹² is each independently selected from the group consisting of hydrogen, alkyl, alkenyl, alkynyl, cycloalkyl, heterocycloalkyl, aryl, heteroaryl, and aralkyl or together form a heteroaryl, or heterocycloalkyl;
R¹³ and R¹⁴ is each independently selected from the group consisting of hydrogen, alkyl, alkenyl, alkynyl, cycloalkyl, heterocycloalkyl, alkoxy, aryl, aralkyl, heteroaryl, and —NR¹¹R¹²; and
A is selected from the group consisting of alkyl, alkenyl, cycloalkyl, alkoxy, alkoxyalkyl, heterocycloalkyl, an alicyclic system, aryl and heteroaryl; optionally substituted.

In above formulas (I), (II), (III), and (IV) the substituents R¹, R², R³, R⁴, R⁵, R⁶, R⁷, R⁸, R⁹, R¹⁰, R¹¹, R¹², R¹³, R¹⁴, and A have the preferred and particularly preferred meanings indicated above with respect to the method of isolating an antagonist. The term antagonist has the meaning as defined above.

The following figures and examples are merely illustrative of the present invention and should not be construed to limit the scope of the invention as indicated by the appended claims in any way.

BRIEF DESCRIPTION OF THE TABLES AND FIGURES

FIG. 1 Chemical structures of the TAS2R38 antagonists. The N—C═S moiety is highlighted by a red circle.

Figure 2:
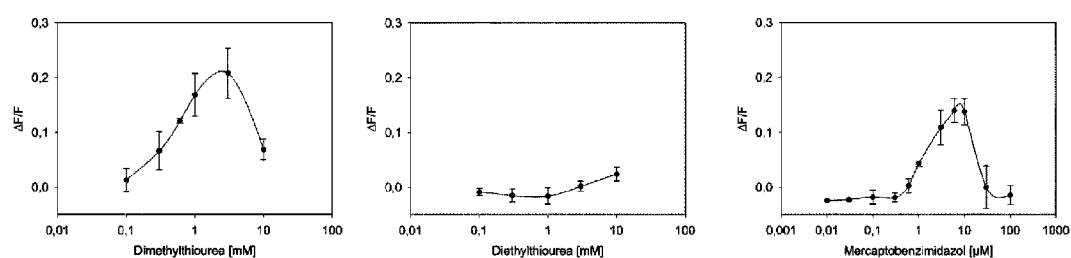

FIG. 2 Averaged (n=3) concentrations responses of the TAS2R38 antagonists on cells transfected with TAS2R38-PAV cDNA.

Figure 3:
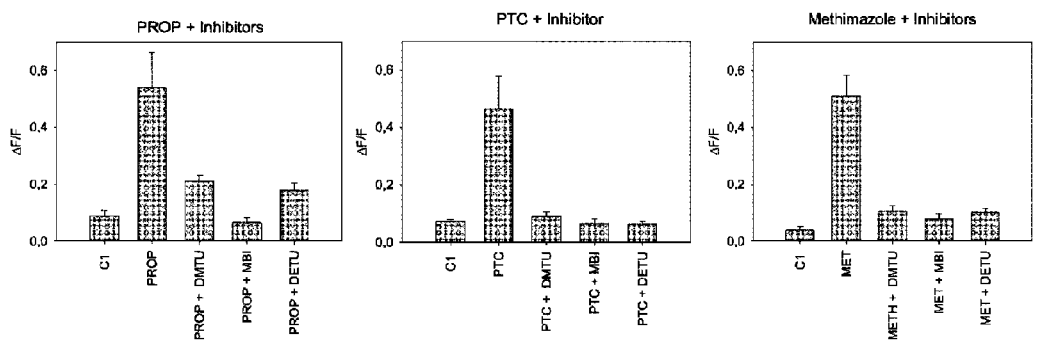

FIG. 3 TAS2R38 antagonists inhibit the responses of TAS2R38 transfected cells to structurally divergent TAS2R38 agonists. Cells were stimulated with 0.03 mM propylthiouracil (PROP), 0.03 mM Phenylthiourea (PTC) or 1 mM methimidazole (MET) either alone or in combination with 20 mM dimethlythiourea (DMTU), 5 mM diethylthiourea (DETU) or 0.1 mM mercaptobenzimidazole (MBI). C1 denotes the response upon mock stimulation with bath solution. Similar results were obtained in two additional experiments.

Figure 4:
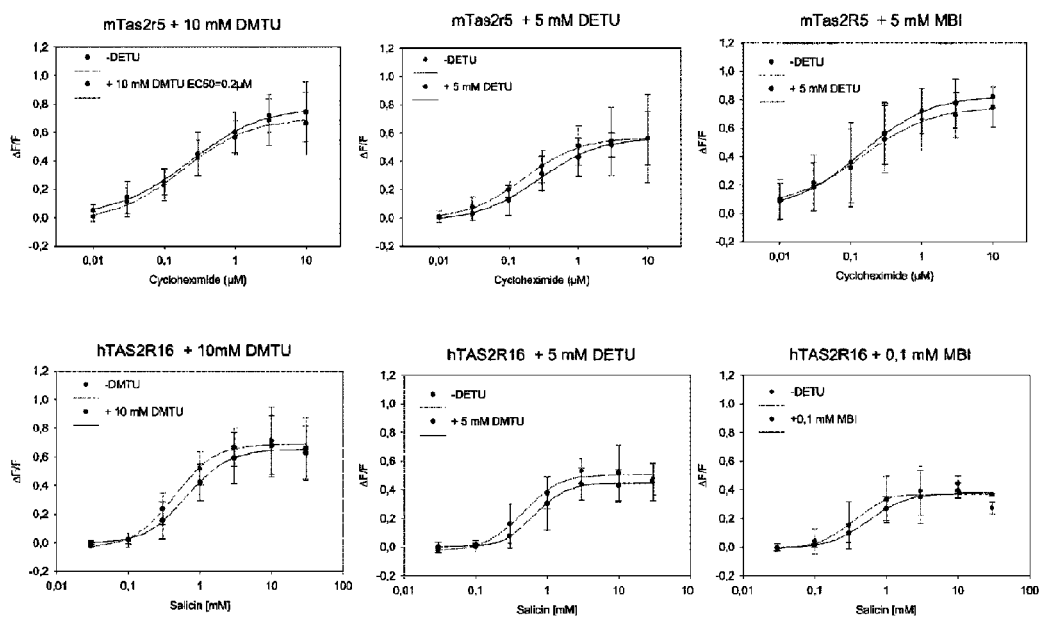

FIG. 4 TAS2R38 antagonists do not alter the response of hTAS2R16 or mTas2r5 transfected cells. TAS2R16 and Tas2r5 transfected cells were stimulated with different salicin and cycloheximide concentrations either alone or as a mixture with 10 mM dimethylthiourea (DMTU), 5 mM diethylthiourea (DETU) or 0.1 mM mercaptobenzimidazole (MBI). Data are averaged over at least three experiments.

Figure 5:
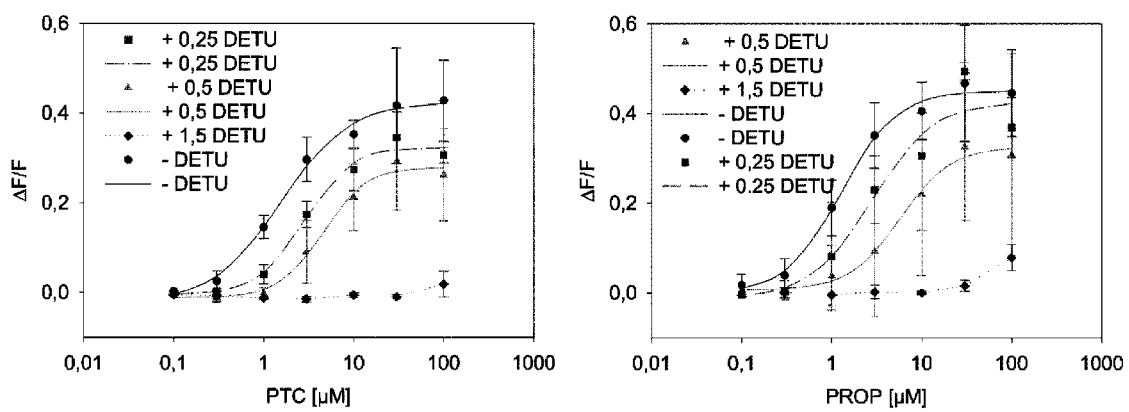

FIG. 5 Averaged effects (n≥3) of different diethylthiourea concentrations (DETU) on the response of TAS2R38 transfected cells upon stimulation with propylthiouracil (PROP), or Phenylthiourea (PTC).

EXAMPLES

Example 1

Human TAS2R38 cDNAs encoding the PAV form of the receptor was fused with a plasma membrane-targeting sequence of the rat somatostatin type 3 receptor at the N terminus of the recombinant polypeptide and a herpes simplex virus glycoprotein D (HSV) epitope at its C terminus (Bufe B., et al. (2002) Nat Genet 32:397-401). The constructs were transiently transfected into human embryonic kidney (HEK)-293T cells that stably express the chimeric G-protein subunit G16gust44 (Ueda T., et al. (2003) J Neurosci 23:7376-7380) using Lipofectamine 2000 (Invitrogen). They were then seeded at a density of ~20-30% and transfected at ~60% confluency in 96-well microtiter plate (Greiner) coated with 10 µg/ml Poly-D-lysine (Sigma-Aldrich). Calcium imaging experiments using an automated fluorometric imaging plate reader (FLIPR) (Molecular Devices) have been performed 24-32 h later essentially as described previously (Bufe B., et al. (2005) Curr. Biol. 15, 322-327). Tastants (Sigma-Aldrich) were dissolved and administered in the following solution: 130 mM NaCl, 5 mM KCl, 10 mM HEPES, 2 mM CaCl2, and 10 mM glucose, pH 7.4. Data were averaged over several independent experiments and processed with SigmaPlot (SPSS). For calculation of dose-response curves, the peak fluorescence responses after addition of compounds were corrected for and normalized to background fluorescence ($\Delta F/F=(F-F_0)/F_0$), and baseline noise was subtracted.

Example 2

During the structure-function-analysis of TAS2R38 agonists we identified and tested various compounds that contain an N—C=S moiety, which is a hallmark of TAS2R38 agonists. Interestingly, diethylthiourea, although it has the N—C=S moiety (FIG. 1), did not activate the receptor at any tested concentration (FIG. 2). Two other compounds, dimethylthiourea and mercaptobenzimidazole that also have an N—C=S moiety (FIG. 1) could activate the receptor only at low to concentrations ($EC_{50}$ of 0.5 mM for dimethylthiourea and 1.0 μM for mercaptobenzimidazole). Application of dimethylthiourea in concentrations above 3 mM led to a dose dependant reduction of the signal amplitude (FIG. 2). Similarly, application of mercaptobenzimidazole in concentrations above 10 μM pronouncedly reduced the response of TAS2R38 receptor expressing cells (FIG. 2).

Example 3

To test whether dimethylthiourea, diethylthiourea and mercaptobenzimidazole are capable of inhibiting the response of other TAS2R38 agonists we next tested them as mixtures with the structurally divergent TAS2R38 agonists propylthiouracil, phenylthiourea and methimidazole. Notably, when applied as a mixture with agonists, diethylthiourea, dimethylthiourea and mercaptobenzimidazole inhibited the responses of all tested agonist (FIG. 3).

Example 4

To examine if the inhibition was specific for TAS2R38 or if other bitter receptors were also inhibited we next tested these antagonists on cells transfected with either hTAS2R16 or mTas2r5. In contrast to the observed effects on TAS2R38, the response of cells expressing hTAS2R16 or mTas2r5 to their cognate ligands salicin or cycloheximide was not altered by any of the three TAS2R38 antagonists in concentrations that inhibited response of TAS2R38 (FIG. 4). This demonstrates that the inhibitory effect of diethylthiourea, dimethylthiourea and mercaptobenzimidazole is TAS2R38 specific.

Example 5

To further investigate the mechanism of the inhibition of TAS2R38 we examined the effect of increasing diethylthiourea concentrations on the dose response curves of propylthiouracil and phenylthiourea (FIG. 5). Increasing concentrations of diethylthiourea lead to a clear right shift of the $EC_{50}$ values for phenylthiourea ($EC_{50}$ of phenylthiourea alone 1.4±0.9 μM, phenylthiourea+0.25 mM diethylthiourea 2.8±0.8 μM, and phenylthiourea+0.5 mM diethylthiourea 4.8±1.8 μM). A similar result was obtained for propylthiouracil ($EC_{50}$ of phenylthiourea alone 1.1±0.8 μM, phenylthiourea+0.25 mM diethylthiourea 3.4±2.5 μM, and phenylthiourea+0.5 mM diethylthiourea 6.3±3.9 μM). Notably, the right shift in $EC_{50}$ values was also accompanied a pronounced reduction of the signal amplitudes that could not be abolished by increasing agonist concentrations (FIG. 5). The clear reduction of the maximal obtainable signal amplitudes suggests that diethylthiourea acts as an allosteric inhibitor of PROP and PTC. This in turn suggests that inhibitory binding site is different from the agonist binding site of PROP and PTC. Thus, the likeliest explanation for the observed right shift in the $EC_{50}$ values caused by negative cooperativity of the inhibitor binding site on the agonist binding site of PROP and PTC.

The invention claimed is:

1. A method for identifying an antagonist of a bitter taste receptor activity, wherein the bitter taste receptor comprises:
   (a) a polypeptide comprising the amino acid sequence according to SEQ ID NO: 2;
   (b) a polypeptide derivative comprising not more than fifteen (15) amino acid residues that are conservatively substituted compared to a polypeptide comprising the amino acid sequence according to SEQ ID NO:2; or
   (c) a polypeptide comprising an amino acid sequence that is at least 90% identical to the amino acid sequence according to SEQ ID NO:2;
   wherein said method comprises:
   (1) contacting the bitter taste receptor or a host cell expressing the bitter taste receptor with a potential antagonist and/or a pharmaceutically acceptable salt thereof having a structure according to formula (I) and/or is a tautomer thereof,

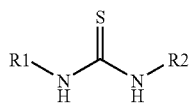

(I)

wherein;
   $R^1$ is selected from the group consisting of alkyl, alkenyl, alkynyl, cycloalkyl, alkoxy, alkoxyalkyl, heterocycloalkyl, an alicyclic system, aryl, and heteroaryl, optionally substituted;
   $R^2$ is selected from the group consisting of alkyl, alkenyl, alkynyl, cycloalkyl, alkoxy, alkoxyalkyl, heterocycloalkyl, an alicyclic system, aryl, and heteroaryl, optionally substituted;
   or
   $R^1$ and $R^2$ together form a heterocycloalkyl, an alicyclic system, or heteroaryl;
   (2) determining whether the potential antagonist inhibits the bitter taste receptor activity;
   (3) identifying a potential antagonist that reduces the activity of the bitter taste receptor when stimulated by an agonist of the bitter taste receptor,
   wherein prior, concomitantly and/or after (1), said bitter taste receptor and/or said host cell is contacted with an agonist of the bitter taste receptor.

2. The method of claim 1, wherein the agonist of the bitter taste receptor is selected from the group consisting of acethylthiourea, N,N-dimethylthioformamide, N,N'-diphenylthiourea, N,N'-ethylene-thiourea, N-ethylthiourea, methimazol, 4(6)-methyl-2-thiouracil, N-methylthiourea, phenylthiocarbamide (PTC), 6-phenyl-2-thiouracil, 5-propyl-2-thiouracil, 6-propyl-2-thiouracil (PROP), tetramethylthiourea, thioacetamide, thioacetanilid, and 2-thiobarbituric acid.

3. The method of claim 1, wherein $R^1$ and $R^2$ are identical.

4. The method of claim 1, wherein the potential bitter taste receptor antagonist has a structure according to formula (II) and/or formula (III), or is a tautomer thereof:

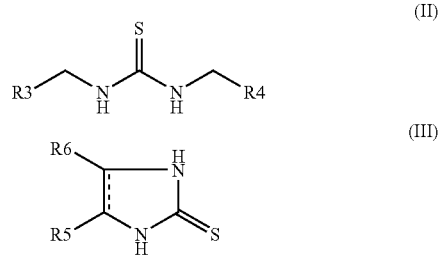

wherein
$R^3$ is selected from the group consisting of hydrogen, alkyl, alkenyl, alkynyl, cycloalkyl, alkoxy, alkoxyalkyl, heterocycloalkyl, an alicyclic system, aryl, and heteroaryl, optionally substituted;
$R^4$ is selected from the group consisting of hydrogen, alkyl, alkenyl, alkynyl, cycloalkyl, alkoxy, alkoxyalkyl, heterocycloalkyl, an alicyclic system, aryl, and heteroaryl, optionally substituted;
$R^5$ is selected from the group consisting of hydrogen, halogen, $-NO_2$, $-CN$, alkyl, alkenyl, cycloalkyl, alkoxy, alkoxyalkyl, heterocycloalkyl, an alicyclic system, aryl, and heteroaryl, optionally substituted;
$R^6$ is selected from the group consisting of alkyl, alkenyl, cycloalkyl, alkoxy, alkoxyalkyl, heterocycloalkyl, an alicyclic system, aryl, and heteroaryl, optionally substituted;
or wherein $R^3$ and $R^4$ together form a heterocycloalkyl, or an alicyclic system;
or wherein $R^5$ and $R^6$ together form a cycloalkyl, heterocycloalkyl, an alicyclic system, aryl, or heteroaryl; and the bond indicated by the dashed line may be present or not.

5. The method of claim 1, wherein the potential antagonist has a structure according to formula (IV) and/or is a tautomer thereof:

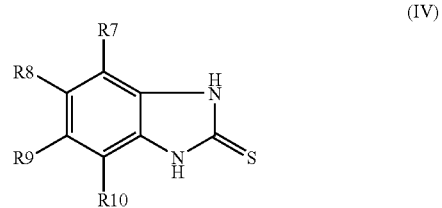

(IV)

wherein
$R^7$, $R^8$, $R^9$ and $R^{10}$ are in each instance independently selected from the group consisting of hydrogen, halogen, $-NO_2$, $-CN$, $-OR^{13}$, $-NR^{11}R^{12}$, $-COOR^{13}$, $-CONR^{11}R^{12}$, $-NR^{11}COR^{13}$, $NR^{11}COR^{13}$, $-NR^{11}CONR^{11}R^{12}$, $-NR^{11}SO_2A$, $-COR^{13}$, $-SO_2NR^{11}R^{12}$, $-OOCR^{13}$, $-CR^{13}R^{14}OH$, $R^{13}OH$, and A;
$R^{11}$ and $R^{12}$ is each independently selected from the group consisting of hydrogen, alkyl, alkenyl, alkynyl, cycloalkyl, heterocycloalkyl, aryl, heteroaryl, and aralkyl or together form a heteroaryl, or heterocycloalkyl;

$R^{13}$ and $R^{14}$ is each independently selected from the group consisting of hydrogen, alkyl, alkenyl, alkynyl, cycloalkyl, heterocycloalkyl, alkoxy, aryl, aralkyl, heteroaryl, and —$NR^{11}R^{12}$; and A is selected from the group consisting of alkyl, alkenyl, cycloalkyl, alkoxy, alkoxyalkyl, heterocycloalkyl, an alicyclic system, aryl, and heteroaryl, optionally substituted.

6. A method for the production of a modified antagonist of the bitter taste receptor of claim 1, wherein the antagonist identified in the method according to claim 1 is N,N'-diethylthiourea, N,N'-dimethylthiourea, and/or 2-mercaptobenzimidazole that is modified by the addition and/or exchange of at least one substituent.

7. The method according to claim 6, wherein the modified antagonist that is selected reduces the activity of the bitter taste receptor when stimulated by an agonist of the bitter taste receptor and/or a structurally related agonist at least as well as the identified antagonist, N,N'-diethylthiourea, N,N'-dimethylthiourea and/or 2-mercaptobenzimidazole, at the same molar concentration.

8. The method according to claim 6, wherein the concentration of N,N'-dimethylthiourea is at least 3 mM and the concentration of 2-mercaptobenzimidazole is at least 0.01 mM.

9. The method of claim 5, wherein $R^7$, $R^8$, $R^9$, and $R^{10}$ in each instance is independently a halogen selected from the group consisting of F, Cl, Br, and I.

* * * * *

SEQUENCE LISTING

<160> NUMBER OF SEQ ID NOS: 2

<210> SEQ ID NO 1
<211> LENGTH: 1002
<212> TYPE: DNA
<213> ORGANISM: Homo sapiens

<400> SEQUENCE: 1

```
atgttgactc taactcgcat ccgcactgtg tcctatgaag tcaggagtac atttctgttc      60
atttcagtcc tggagtttgc agtggggttt ctgaccaatg ccttcgtttt cttggtgaat     120
ttttgggatg tagtgaagag gcagccactg agcaacagtg attgtgtgct gctgtgtctc     180
agcatcagcc ggcttttcct gcatggactg ctgttcctga gtgctatcca gcttacccac     240
ttccagaagt tgagtgaacc actgaaccac agctaccaag ccatcatcat gctatggatg     300
attgcaaacc aagccaacct ctggcttgct gcctgcctca gcctgctttta ctgctccaag     360 ctcatccgtt tctctcacac cttcctgatc tgcttggcaa gctgggtctc caggaagatc     420
tcccagatgc tcctgggtat tattctttgc tcctgcatct gcactgtcct ctgtgtttgg     480 tgcttttta gcagacctca cttcacagtc acaactgtgc tattcatgaa taacaataca     540
aggctcaact ggcagattaa agatctcaat ttattttatt cctttctctt ctgctatctg     600
tggtctgtgc ctcctttcct attgtttctg gtttcttctg ggatgctgac tgtctccctg     660
```

-continued

```
ggaaggcaca tgaggacaat gaaggtctat accagaaact ctcgtgaccc cagcctggag    720
gcccacatta aagccctcaa gtctcttgtc tccttttttct gcttctttgt gatatcatcc    780
tgtgctgcct tcatctctgt gcccctactg attctgtggc gcgacaaaat aggggtgatg    840
gtttgtgttg ggataatggc agcttgtccc tctgggcatg cagccgtcct gatctcaggc    900
aatgccaagt tgaggagagc tgtgatgacc attctgctct gggctcagag cagcctgaag    960
gtaagagccg accacaaggc agattcccgg acactgtgct ga                      1002
```

<210> SEQ ID NO 2
<211> LENGTH: 333
<212> TYPE: PRT
<213> ORGANISM: Homo sapiens

<400> SEQUENCE: 2

```
Met Leu Thr Leu Thr Arg Ile Arg Thr Val Ser Tyr Glu Val Arg Ser
 1               5                  10                  15

Thr Phe Leu Phe Ile Ser Val Leu Glu Phe Ala Val Gly Phe Leu Thr
            20                  25                  30

Asn Ala Phe Val Phe Leu Val Asn Phe Trp Asp Val Val Lys Arg Gln
        35                  40                  45

Pro Leu Ser Asn Ser Asp Cys Val Leu Leu Cys Leu Ser Ile Ser Arg
    50                  55                  60

Leu Phe Leu His Gly Leu Leu Phe Leu Ser Ala Ile Gln Leu Thr His
65                  70                  75                  80

Phe Gln Lys Leu Ser Glu Pro Leu Asn His Ser Tyr Gln Ala Ile Ile
                85                  90                  95

Met Leu Trp Met Ile Ala Asn Gln Ala Asn Leu Trp Leu Ala Ala Cys
            100                 105                 110

Leu Ser Leu Leu Tyr Cys Ser Lys Leu Ile Arg Phe Ser His Thr Phe
        115                 120                 125

Leu Ile Cys Leu Ala Ser Trp Val Ser Arg Lys Ile Ser Gln Met Leu
    130                 135                 140

Leu Gly Ile Ile Leu Cys Ser Cys Ile Cys Thr Val Leu Cys Val Trp
145                 150                 155                 160

Cys Phe Phe Ser Arg Pro His Phe Thr Val Thr Val Leu Phe Met
                165                 170                 175

Asn Asn Asn Thr Arg Leu Asn Trp Gln Ile Lys Asp Leu Asn Leu Phe
            180                 185                 190

Tyr Ser Phe Leu Phe Cys Tyr Leu Trp Ser Val Pro Pro Phe Leu Leu
        195                 200                 205

Phe Leu Val Ser Ser Gly Met Leu Thr Val Ser Leu Gly Arg His Met
    210                 215                 220

Arg Thr Met Lys Val Tyr Thr Arg Asn Ser Arg Asp Pro Ser Leu Glu
225                 230                 235                 240

Ala His Ile Lys Ala Leu Lys Ser Leu Val Ser Phe Phe Cys Phe Phe
                245                 250                 255

Val Ile Ser Ser Cys Ala Ala Phe Ile Ser Val Pro Leu Leu Ile Leu
            260                 265                 270

Trp Arg Asp Lys Ile Gly Val Met Val Cys Val Gly Ile Met Ala Ala
        275                 280                 285

Cys Pro Ser Gly His Ala Ala Val Leu Ile Ser Gly Asn Ala Lys Leu
    290                 295                 300

Arg Arg Ala Val Met Thr Ile Leu Leu Trp Ala Gln Ser Ser Leu Lys
305                 310                 315                 320
```

```
Val Arg Ala Asp His Lys Ala Asp Ser Arg Thr Leu Cys
            325                 330
```